(12) United States Patent
Woollam et al.

(10) Patent No.: US 7,385,697 B2
(45) Date of Patent: Jun. 10, 2008

(54) SAMPLE ANALYSIS METHODOLOGY UTILIZING ELECTROMAGNETIC RADIATION

(75) Inventors: John A. Woollam, Lincoln, NE (US); Corey L. Bungay, Lincoln, NE (US); Thomas E. Tiwald, Lincoln, NE (US); Martin M. Liphardt, Lincoln, NE (US); Ronald A. Synowicki, Lincoln, NE (US); Gregory K. Pribil, Lincoln, NE (US); Craig M. Herzinger, Lincoln, NE (US); Blaine D. Johs, Lincoln, NE (US); James N. Hilfiker, Lincoln, NE (US)

(73) Assignee: J.A. Woollam Co., Inc., Lincoln, NE (US)

( * ) Notice: Subject to any disclaimer, the term of this patent is extended or adjusted under 35 U.S.C. 154(b) by 577 days.

(21) Appl. No.: 10/849,740

(22) Filed: May 20, 2004

(65) Prior Publication Data

US 2004/0257567 A1    Dec. 23, 2004

Related U.S. Application Data

(63) Continuation-in-part of application No. 10/713,816, filed on Nov. 17, 2003, and a continuation-in-part of application No. 10/376,677, filed on Feb. 28, 2003, now Pat. No. 6,982,792.

(60) Provisional application No. 60/471,769, filed on May 20, 2003, provisional application No. 60/485,009, filed on Jul. 5, 2003, provisional application No. 60/527,553, filed on Dec. 6, 2003.

(51) Int. Cl.
*G01J 4/00* (2006.01)
(52) U.S. Cl. ..................................... 356/369
(58) Field of Classification Search ................ 356/364, 356/369
See application file for complete search history.

(56) References Cited

U.S. PATENT DOCUMENTS 7,110,912 B1 * 9/2006 Tiwald ....................... 702/170

OTHER PUBLICATIONS

Muller, Rolf H., Ellipsometry as an in Situ Probe for the Study of Electrode Processes, Techniques for Characterization of Electrodes and Electrochemical Processes, 1991, pp. 31-125, John Wiley & Sons, Inc., United States of America.

Rudnicki, James D., McLarnon, Frank R., Cairns, and Elton J., In Situ Characterization of Electrode Processes by Photothermal Deflection Spectroscopy, Techniques for Characterization of Electrodes and Electrochemical Processes, 1991, pp. 127-166, John Wiley & Sons, Inc., United States of America.

Johs, B., Hales, J., Herzinger, C., Doctor, D., Elliott, K., Olson, G., Chow, D., Roth, J., Ferguson, I., Pelczynski, M., Kuo, C.H., and Johnson, S., Real-Time Monitoring of Semiconductor Growth by Spectroscopic Ellipsometry, In Situ Process Diagnostics and Intelligent Materials Processing, 1998, pp. 3-14, 502, Materials Research Society, United States of America.

(Continued)

*Primary Examiner*—Roy M. Punnoose
(74) *Attorney, Agent, or Firm*—James D. Welch

(57) ABSTRACT

Simultaneous use of wavelengths in at least two ranges selected from RADIO, MICRO, FIR, IR, NIR-VIS-NUV, UV, DUV, VUV EUV, XRAY in a regression procedure to evaluate parameters in mathematical dispersion structures to model dielectric functions.

25 Claims, 11 Drawing Sheets

OTHER PUBLICATIONS

Solomon, P.R., Charpenay, S., Zhang, W., Bonanno, A.S., Rosenthal, P.A., Cosgrove, J.E., Kinsella, K.K., and Kung, P.J., In-Situ Fourier Transform Infrared Spectroscopy for Real-Time Diagnostics of Thin Film Processes, In Situ Process Diagnostics and Intelligent Materials Processing, 1998, pp. 15-22, 502, Materials Research Society, United States of America.

Collins, R.W., Lee, J., Rovira, P.I., and An, I., Rotating-Compensator Multichannel Ellipsometry: Applications in Process Development for Nanocrystalline Diamond Thin Films, In Situ Process Diagnostics and Intelligent Materials Processing, 1998, pp. 23-34, 502, Materials Research Society, United States of America.

Parent, T., Heitz, R., Chen, P., and Madhukar, A., Real-Time Feedback Control of Thermal CL2 Etching of GaAs Based on In Situ Spectroscopic Ellipsometry, In Situ Process Diagnostics and Intelligent Materials Processing, 1998, pp. 71-76, 502, Materials Research Society, United States of America.

Bungay, C.L., Tiwald, T.E., DeVries, M.J., Dworak, B.J., and Woollam, J.A., In Situ and Ex Situ Ellipsometric Characterization of Oxygen Plasma and UV Radiation Effects on Spacecraft Materials, In Situ Process Diagnostics and Intelligent Materials Processing, 1998, pp. 177-183, 502, Materials Research Society, United States of America.

Blank, Dave H.A. and Rogalla, Horst., In-Situ Diagnostics at High Pressures: Ellipsometric and Rheed Studies of the Growth of YBa2Cu3O7, In Situ Process Diagnostics and Intelligent Materials Processing, 1998, pp. 237-247, 502, Materials Research Society, United States of America.

Simmons, Joseph H. and Potter, Kelly S., Ligand Field Theory Concepts Appendix 3C, Optical Materials, 2000, pp. 155-158, Academic Press, United States of America.

Simmons, Joseph H. and Potter, Kelly S., Impurity states and lattice imperfections. 5.5.3 Excitons, Optical Materials, 2000, pp. 212-214, Academic Press, United States of America.

Simmons, Joseph H. and Potter, Kelly S., Materials and properties. 5.9.1 Fabrication and growth, Optical Materials, 2000, pp. 247-252, Academic Press, United States of America.

Simmons, Joseph H. and Potter, Kelly S., Materials and properties. 5.9.2 Color, Optical Materials, 2000, pp. 253-254, Academic Press, United States of America.

Simmons, Joseph H. and Potter, Kelly S., Semiconductor Lasers. 6.9.3 Heterojunction lasers, Optical Materials, 2000, pp. 321-322, Academic Press, United States of America.

Woollam, John A., Bungay, Corey, Hilfiker, James, N., Johs, Blaine, Yan, Li., Spectroscopic ellipsometry in plasma deposited and plasma modified materials, The Seventh International Symposium on Sputtering and Plasma Process (ISSP 2003), Jun. 2003, pp. 33-38, Eiji Setoyama, Japan.

Lee, Joungchel, Spectroscopic Ellipsometry Studies of Wide Band Gap Semiconducting Materials, 1997, pp. 19-24, UMI Company, United States of America.

Lee, Joungchel, Spectroscopic Ellipsometry Studies of Wide Band Gap Semiconducting Materials, 1997, pp. 32-41, UMI Company, United States of America.

Koh, Joohyun, Real Time Spectroscopic Ellipsometry Study for the Design and Optimization of Hydrogenated Amorphous Silicon-Based Solar Cells, 1998, pp. 7-12, UMI Company, United States of America.

Roseler, Arnulf, Infrared Spectropscopic Ellipsometry, 1990, pp. 103-108, Akademi-Verlag Berlin, Germany.

Azzam, R.M.A. and Bashara, N.M., Ellipsometry and Polarized Light, 1987, pp. 148-152, Elsevier Science Publishing Co., Inc., United States of America.

Azzam, R.M.A. and Bashara, N.M., Ellipsometry and Polarized Light, 1987, pp. 376-386, Elsevier Science Publishing Co., Inc., United States of America.

Brundle, C. Richard, Evans, Jr., Charles, A., and Wilson, Shaun., Encyclopedia of Materials Characterization, 1992, pp. 282-299, Manning Publications Co., United States of America.

Brundle, C. Richard, Evans, Jr., Charles, A., and Wilson, Shaun., Encyclopedia of Materials Characterization, 1992, pp. 401-411, Manning Publications Co., United States of America.

Brundle, C. Richard, Evans, Jr., Charles, A., and Wilson, Shaun., Encyclopedia of Materials Characterization, 1992, pp. 416-427, Manning Publications Co., United States of America.

Brundle, C. Richard, Evans, Jr., Charles, A., and Wilson, Shaun., Encyclopedia of Materials Characterization, 1992, pp. 698-710, Manning Publications Co., United States of America.

Azzam, R.M.A. (editor), Vasicek, A., Historical Remarks on the Drude Formulae, Selected Papers on Ellipsometry, 1991, p. 11, vol. MS 27, SPIE-The International Society for Optical Engineering, United States of America.

Azzam, R.M.A. (editor), Drude, P., Ueber oberflachenschichten, I. Thiel, Selected Papers on Ellipsometry, 1991, pp. 41-55, vol. MS 27, SPIE-The International Society for Optical Engineering, United States of America.

Azzam, R.M.A. (editor), Tronstad, L., The validity of Drude's optical method of investigating transparent films on metal, Selected Papers on Ellipsometry, 1991, pp. 97-99, vol. MS 27, SPIE-The International Society for Optical Engineering, United States of America.

Azzam, R.M.A. (editor), Kruger, J. and Ambs, W.J., Optical measurements on thin films of condensed gases at lower temperatures, Selected Papers on Ellipsometry, 1991, pp. 127-130, vol. MS 27, SPIE-The International Society for Optical Engineering, United States of America.

Azzam, R.M.A. (editor), Archer, R.J. and Gobeli, G.W., Measurement of oxygen adsorption on silicon by ellipsometry, Selected Papers on Ellipsometry, 1991, pp. 154-162, vol. MS 27, SPIE-The International Society for Optical Engineering, United States of America.

Azzam, R.M.A. (editor),Yeh, P., Optics on anisotropic layered media: A new 4×4 matrix algebra, Selected Papers on Ellipsometry, 1991, pp. 183-189, vol. MS 27, SPIE-The International Society for Optical Engineering, United States of America.

Azzam, R.M.A. (editor), den Engelsen, D., Ellipsometry of Anisotropic Films, Selected Papers on Ellipsometry, 1991, pp. 257-263, vol. MS 27, SPIE-The International Society for Optical Engineering, United States of America.

Azzam, R.M.A. (editor), So, S.S. and Vedam, K., Generalized ellipsometric method for the absorbing substrate covered with a transparent film system. Optical constants of silicon on 3655 A., Selected Papers on Ellipsometry, 1991, pp. 264-271, vol. MS 27, SPIE-The International Society for Optical Engineering, United States of America.

Azzam, R.M.A. (editor), Muller, R.H. and Smith, C.G., Use of film-formation models for the interpretation of ellipsometer observations, Selected Papers on Ellipsometry, 1991, pp. 299-311, vol. MS 27, SPIE-The International Society for Optical Engineering, United States of America.

Azzam, R.M.A. (editor), Rasing, Th., Hsiung, H., Shen, Y.R., and Kim, M.W., Ellipsometry study of two-dimensional phase transitions, Selected Papers on Ellipsometry, 1991, pp. 331-334, vol. MS 27, SPIE-The International Society for Optical Engineering, United States of America.

Azzam, R.M.A. (editor), Hauge, P.S., Recent developments in instrumentation in ellipsometry, Selected Papers on Ellipsometry, 1991, pp. 337-353, vol. MS 27, SPIE-The International Society for Optical Engineering, United States of America.

Azzam, R.M.A. (editor), Beattie, J.R., Optical constants of metals in the infrared-experimental methods, Selected Papers on Ellipsometry, 1991, pp. 365-370, vol. MS 27, SPIE-The International Society for Optical Engineering, United States of America.

Azzam, R.M.A. (editor), Faber, T.E. and Smith N.V., Optical measurements on liquid metals using a new ellipsometer, Selected Papers on Ellipsometry, 1991, pp. 382-388, vol. MS 27, SPIE-The International Society for Optical Engineering, United States of America.

Azzam, R.M.A. (editor), Cahan, B.D. and Spanier, R.F., A high speed precision automatic ellipsometer, Selected Papers on Ellipsometry, 1991, pp. 396-401, vol. MS 27, SPIE-The International Society for Optical Engineering, United States of America.

Azzam, R.M.A. (editor), Stobie, R.W., Rao, B., and Dignam, M.J., Analysis of a novel ellipsometric technique with special advantages for infrared spectroscopy, Selected Papers on Ellipsometry, 1991, pp. 434-442, vol. MS 27, SPIE-The International Society for Optical Engineering, United States of America.

Azzam, R.M.A. (editor), Moritani, A., Okuda, Y., and Nakai, J., A retardation modulation ellipsometer for studying fast surface transients, Selected Papers on Ellipsometry, 1991, pp. 452-454, vol. MS 27, SPIE-The International Society for Optical Engineering, United States of America.

Azzam, R.M.A. (editor), Hazebroek, H.F. and Holscher, A.A., Interferometric ellipsometry, Selected Papers on Ellipsometry, 1991, pp. 465-469, vol. MS 27, SPIE-The International Society for Optical Engineering, United States of America.

Azzam, R.M.A. (editor), Holmes, D.A. and Feucht, D.L., Formulas for using wave plates in ellipsometry, Selected Papers on Ellipsometry, 1991, pp. 501-507, vol. MS 27, SPIE-The International Society for Optical Engineering, United States of America.

Azzam, R.M.A. (editor), Erman, M. and Theeten, J.B., Spatially resolved ellipsometry, Selected Papers on Ellipsometry, 1991, pp. 554-568, vol. MS 27, SPIE-The International Society for Optical Engineering, United States of America.

Azzam, R.M.A. (editor), Barsukov, D.O., Gusakov, G.M., and Komarnitskii, A.A., Precision ellipsometry based on a focused light beam. Part 1, Selected Papers on Ellipsometry, 1991, pp. 569-572, vol. MS 27, SPIE-The International Society for Optical Engineering, United States of America.

Azzam, R.M.A. (editor), Roseler, A., Spectroscopic ellipsometry in the infrared, Selected Papers on Ellipsometry, 1991, pp. 645-651, vol. MS 27, SPIE-The International Society for Optical Engineering, United States of America.

Azzam, R.M.A. (editor), DeNicola, R.O., Saifi, M.A., and Frazee, R.E., Epitaxial layer thickness measurement by far infrared ellipsometry, Selected Papers on Ellipsometry, 1991, pp. 687-699, vol. MS 27, SPIE-The International Society for Optical Engineering, United States of America.

G.Crean, R. Struck, and J. Woollam (editors), Maracas, G.N., Edwards, J.L, Gerber, D.S., and Droopad, R., In situ spectroscopic ellipsometry in molecular beam epitaxy for photonic devices, Semiconductor Materials Analysis and Fabrication Process Control, 1993, pp. 1-8, vol. 34, Elsevier Science Publishers B.V., The Netherlands.

Hilfiker, J.N., Hale, J.S., Johs, B.D., Tiwald, T.E., Synowicki, R.A., Bungay, C.L., and Woollam, J.A., Spectroscopic ellipsometry in optical coatings manufacturing, Society of Vacuum Coaters 44th Annual Technical Conference Proceedings, 2001, pp. 295-300, Society of Vacuum Coaters, United States of America.

Exarhos, G.J., Guenther, A.H., Kaiser, N., Lewis, K.L., Soileau, M.J., Stolz, C.J., Giesen, A., and Weber, H. (editors), Woollam, John A., Bungay, Corey, Yan, Li, Thompson, Dan W., and Hilfiker, James., Application of spectroscopic ellipsometry to characterization of optical thin films, Laser-Induced Damage in Optical Materials: 2002 and 7th International Workshop on Laser Beam and Optics Characterization, 2002, pp. 393-404, vol. 4932, SPIE-The International Society for Optical Engineering, United States of America.

Seiler, D.G., Diebold, A.C., Shaffner, T.J., McDonald, R., Zollner, S., Khosla, R.P., and Secula, E.M. (editors), Boher, P., Evrard, P., Piel, J.P., Defranoux, C., Fouere, J.C., Bellandi, E., and Bender, H., High-k dielectric characterization by VUV spectroscopic ellipsometry and X-ray reflection, Characterization and Metrology for ULSI Technology, 2003, pp. 148-153, vol. 683, American Institute of Physics, United States of America.

Seiler, D.G., Diebold, A.C., Shaffner, T.J., McDonald, R., Zollner, S., Khosla, R.P., and Secula, E.M. (editors), Kim, H.J., Cho, Y.J., Cho, H.M., Kim, S.Y., Moon, C., Cho, G., and Kwon, Y., Optical properties of silicon oxynitride thin films determined by vacuum ultraviolet spectroscopic ellipsometry, Characterization and Metrology for ULSI Technology, 2003, pp. 171-175, vol. 683, American Institute of Physics, United States of America.

Seiler, D.G., Diebold, A.C., Shaffner, T.J., McDonald, R., Zollner, S., Khosla, R.P., and Secula, E.M. (editors), Nguyen, N.V., Han, J.P., Kim, J.Y., Wilcox, E., Cho, Y.J., Zhu, W., Luo, Z., and Ma, T.P., Optical properties of jet-vapor-deposited TiAlO and HfAlO determined by vacuum ultraviolet spectroscopic ellipsometry, Characterization and Metrology for ULSI Technology, 2003, pp. 181-185, vol. 683, American Institute of Physics, United States of America.

Seiler, D.G., Diebold, A.C., Shaffner, T.J., McDonald, R., Zollner, S., Khosla, R.P., and Secula, E.M. (editors), Chandler-Horowitz, D., Nguyen, N.V., and Ehrstein, J.R., Assessment of ultra-thin SiO2 film thickness measurement precision by ellipsometry, Characterization and Metrology for ULSI Technology, 2003, pp. 326-330, vol. 683, American Institute of Physics, United States of America.

Seiler, D.G., Diebold, A.C., Shaffner, T.J., McDonald, R., Zollner, S., Khosla, R.P., and Secula, E.M. (editors), Ehrstein, J., Richter, C., Chandler-Horowitz, D., Vogel, E., Ricks, D., Young, C., Spencer, S., Shah, S., Maher, D., Foran, B., Diebold, A., and Hung, P.Y., Thickness evaluation for 2nm SiO2 films, a comparison of ellipsometric, capacitance-voltage and HRTEM measurements, Characterization and Metrology for ULSI Technology, 2003, pp. 331-336, vol. 683, American Institute of Physics, United States of America.

Seiler, D.G., Diebold, A.C., Shaffner, T.J., McDonald, R., Zollner, S., Khosla, R.P., and Secula, E.M. (editors), Boher, P., Bucchia, M., Guillotin, C., Defranoux, C., and Fouere, J.C., New infrared spectroscopic ellipsometer for low-k dielectric characterization, Characterization and Metrology for ULSI Technology, 2003, pp. 540-545, vol. 683, American Institute of Physics, United States of America.

Seiler, D.G., Diebold, A.C., Shaffner, T.J., McDonald, R., Zollner, S., Khosla, R.P., and Secula, E.M. (editors), Rubloff, G.W., In situ metrology: the path to real-time advanced process control, Characterization and Metrology for ULSI Technology, 2003, pp. 583-591, vol. 683, American Institute of Physics, United States of America.

Seiler, D.G., Diebold, A.C., Shaffner, T.J., McDonald, R., Zollner, S., Khosla, R.P., and Secula, E.M. (editors), Edwards, N.V., Status and prospects for VUV ellipsometry (Applied to high K and low K materials), Characterization and Metrology for ULSI Technology, 2003, pp. 723-737, vol. 683, American Institute of Physics, United States of America.

Seiler, D.G., Diebold, A.C., Shaffner, T.J., McDonald, R., Zollner, S., Khosla, R.P., and Secula, E.M. (editors), Chegal, W., Kim, D., Kim, S., Cho, Y.J., Cho, H.M., and Lee, Y.W., One-dimensional spectroscopic measurement of patterned structures using a custom-built spectral imaging ellipsometer, Characterization and Metrology for ULSI Technology, 2003, pp. 753-757, vol. 683, American Institute of Physics, United States of America.

Seiler, D.G., Diebold, A.C., Bullis, W.M., Shaffner, T.J., McDonald, R., and Walter, E.J. (editors), Richter, C.A., Nguyen, N.V., Dura, J.A., and Majkrzak, C.F., Characterization of thin SiO2 on Si by spectroscopic ellipsometry, neutron reflectometry, and X-ray reflectometry, Characterization and Metrology for ULSI Technology, 1998, pp. 185-189, vol. 449, American Institute of Physics, United States of America.

Seiler, D.G., Diebold, A.C., Bullis, W.M., Shaffner, T.J., McDonald, R., and Walter, E.J. (editors), Alt, H.Ch., Gellon, M., Pretto, M.G., Scala, R., Bittersberger, F., Hesse, K., and Kempf, A., Determination of shallow dopants in silicon by low-temperature FTIR spectroscopy, Characterization and Metrology for ULSI Technology, 1998, pp. 201-205, vol. 449, American Institute of Physics, United States of America.

Seiler, D.G., Diebold, A.C., Bullis, W.M., Shaffner, T.J., McDonald, R., and Walter, E.J. (editors), Chandler-Horowitz, D., Amirtharaj, P.M., and Stoup, J.R., High-resolution, high-accuracy, mid-IR refractive index measurements in silicon, Characterization and Metrology for ULSI Technology, 1998, pp. 207-211, vol. 449, American Institute of Physics, United States of America.

Seiler, D.G., Diebold, A.C., Bullis, W.M., Shaffner, T.J., McDonald, R., and Walter, E.J. (editors), Rosenthal,P., Aarts, W., Bonanno, A., Boning, D., Charpenay, S., Gower, A., Richter, M., Smith, T., Solomon, P., Spartz, M., Nelson, C., Waldhauer, A., Xu, J., Yakovlev, V., Zhang, W., Allen, L., Cordts, B., Brandt, M., Mundt, R and Perry, A., Infrared spectroscopy for process control and fault detection of advanced semiconductor processes, Characterization and Metrology for ULSI Technology, 1998, pp. 213-219, vol. 449, American Institute of Physics, United States of America.

Seiler, D.G., Diebold, A.C., Bullis, W.M., Shaffner, T.J., McDonald, R., and Walter, E.J. (editors), Tiwald, T.E., Miller, A.D., and Woollam, J.A., Measurement of silicon doping profiles using infrared ellipsometry combined with anodic oxidation sectioning, Characterization and Metrology for ULSI Technology, 1998, pp. 221-225, vol. 449, American Institute of Physics, United States of America.

Seiler, D.G., Diebold, A.C., Bullis, W.M., Shaffner, T.J., McDonald, R., and Walter, E.J. (editors), Zollner, S., Liu, R., Christiansen, J., Chen, W., Monarch, K., and Lee, T.C., Optical studies of phosphorus-doped poly-si films, Characterization and Metrology for ULSI Technology, 1998, pp. 298-302, vol. 449, American Institute of Physics, United States of America.

Seiler, D.G., Diebold, A.C., Bullis, W.M., Shaffner, T.J., McDonald, R., and Walter, E.J. (editors), Carline, R.T., Russell, J., Pickering, C., and Hope, D.A.O., Rapid non-invasive temperature measurement of complex Si structures using in situ spectroscopic ellipsometry, Characterization and Metrology for ULSI Technology, 1998, pp. 310-314, vol. 449, American Institute of Physics, United States of America.

Seiler, D.G., Diebold, A.C., Bullis, W.M., Shaffner, T.J., McDonald, R., and Walter, E.J. (editors), Lee, M.E., Galarza, C., Kong, W., Sun, W., and Terry Jr., F.L., Analysis of reflectometry and ellipsometry data from patterned structures, Characterization and Metrology for ULSI Technology, 1998, pp. 331-335, vol. 449, American Institute of Physics, United States of America.

Seiler, D.G., Diebold, A.C., Bullis, W.M., Shaffner, T.J., McDonald, R., and Walter, E.J. (editors), Lehnert, W., Petrik, P., Schneider, C., Pfitzner, R., and Ryssel, H., In situ layer characterization by spectroscopic ellipsometry at high temperatures, Characterization and Metrology for ULSI Technology, 1998, pp. 336-340, vol. 449, American Institute of Physics, United States of America.

Seiler, D.G., Diebold, A.C., Bullis, W.M., Shaffner, T.J., McDonald, R., and Walter, E.J. (editors), Pickering, C., Russell, J., Hope, D.A.O., Carline, R.T., Marrs, A.D., Robbins, D.J., and Dann, A., Instrumental and computational advances for real-time process control using spectroscopic ellipsometry, Characterization and Metrology for ULSI Technology, 1998, pp. 341-345, vol. 449, American Institute of Physics, United States of America.

Seiler, D.G., Diebold, A.C., Bullis, W.M., Shaffner, T.J., McDonald, R., and Walter, E.J. (editors), Pickering, C., Russel, J., Nayar, V., Imschweiler, J., Wille, H., Harrington, S., Wiggins, C., Stehle, J.L., Piel, J.P., and Bruchez, J., Evaluation of an automated spectroscopic ellipsometer for in-line process control, Characterization and Metrology for ULSI Technology, 1998, pp. 347-351, vol. 449, American Institute of Physics, United States of America.

Seiler, D.G., Diebold, A.C., Bullis, W.M., Shaffner, T.J., McDonald, R., and Walter, E.J. (editors), Hilfiker, J.N., Carpio, R, Synowicki, R.A., and Woollam, J.A., Metrology applications in lithography with variable angle spectroscopic ellipsometry, Characterization and Metrology for ULSI Technology, 1998, pp. 543-547, vol. 449, American Institute of Physics, United States of America.

Seiler, D.G., Diebold, A.C., Bullis, W.M., Shaffner, T.J., McDonald, R., and Walter, E.J. (editors), Ager III, J.W., Overview of optical microscopy and optical microspectroscopy, Characterization and Metrology for ULSI Technology, 1998, pp. 641-652, vol. 449, American Institute of Physics, United States of America.

Al-Jumaily, G.A., (editor), Woollam, J.A., Johs, B., Herzinger, C., Hilfiker, J., Synowicki, R., and Bungay, C., Overview of variable angle spectroscopic ellipsometry (VASE), part I: Basic theory and typcial applications, Optical Metrology, 1999, pp. 3-28, vol. CR72, SPIE-The International Society for Optical Engineering, United States of America.

Al-Jumaily, G.A. (editor), Kief, M.T., Insitu ellipsometry-Applications to thin film research, development and production, Optical Metrology, 1999, pp. 78-106, vol. CR72, SPIE-The International Society for Optical Engineering, United States of America.

Al-Jumaily, G.A. (editor), Johs, B., Woollam, J.A., Herzinger, C., Hilfiker, J., Synowicki, R., and Bungay, C., Overview of variable angle spectroscopic ellipsometry (VASE), part II: Advanced Application, Optical Metrology, 1999, pp. 29-58, vol. CR72, SPIE-The International Society for Optical Engineering, United States of America.

Wertheimer, M.R. (editor), Woollam, J.A., Bungay, C., Hilfiker, J., and Tiwald, T., VUV and IR spectroellipsometric studies of polymer surfaces, Ionizing Radiation and Polymers (Proceedings of 5th International Symposium), 2003, pp. 35-39, vol. 208, Elsevier B.V., The Netherlands.

Jansson, R., Line shape analysis of ellipsometric spectra on thin conducting polymer films, Spectroscopic Ellipsometry Instrumentation and Applications, 1993, pp. 119-128, University of Linkoping, Sweden.

Duparre, A. and Singh, B. (editors), Johs, B., Hale, J., Ianno, N.J., Herzinger, C.M., Tiwald, T., and Woollam, J.A., Recent developments in spectroscopic ellipsometry for in situ applications, Optical Metrology Roadmap for the Semiconductor, Optical, and Data Storage Industries II, 2001, pp. 41-57, vol. 4449, SPIE-The International Society for Optical Engineering, United States of America.

Bullis, W.M., Seiler, D.G., and Diebold, A.C. (editors), Perkowitz, S., Seiler, D.G., and Bullis, W.M., Optical characterization of materials and devices for the semiconductor industry: Trends and needs, Semiconductor Characterization Present Status and Future Needs, 1996, pp. 422-427, American Institute of Physics, United States of America.

Bullis, W.M., Seiler, D.G., and Diebold, A.C. (editors), Heyd, A.R., Alterovitz, S.A., Croke, E.T., Wang, K.L., and Lee, C.H., Characterization of SiGe/Ge heterostructures and graded layers using variable angle spectroscopic ellipsometry, Semiconductor Characterization Present Status and Future Needs, 1996, pp. 428-432, American Institute of Physics, United States of America.

Bullis, W.M., Seiler, D.G., and Diebold, A.C. (editors), McGahan, W.A. and Woollam, J.A., Ellipsometric characterization of thin oxides on Silicon, Semiconductor Characterization Present Status and Future Needs, 1996, pp. 433-437, American Institute of Physics, United States of America.

Bullis, W.M., Seiler, D.G., and Diebold, A.C. (editors), Nguyen, N.V., Chandler-Horowitz, D., Pellegrino, J.G., and Amirtharaj, P.M., High-accuracy principal-angle scanning spectroscopic ellipsometry of semiconductor interfaces, Semiconductor Characterization Present Status and Future Needs, 1996, pp. 438-442, American Institute of Physics, United States of America.

Bullis, W.M., Seiler, D.G., and Diebold, A.C. (editors), Duncan, W.M., Bevan, M.J., and Henck, S.A., Real-time spectral ellipsometry applied to semiconductor thin film diagnostics, Semiconductor Characterization Present Status and Future Needs, 1996, pp. 467-475, American Institute of Physics, United States of America.

Bullis, W.M., Seiler, D.G., and Diebold, A.C. (editors), Maracas, G.N. and Kuo, C.H., Real time analysis and control of epitaxial growth, Semiconductor Characterization Present Status and Future Needs, 1996, pp. 476-484, American Institute of Physics, United States of America.

Bullis, W.M., Seiler, D.G., and Diebold, A.C. (editors), Celii, F.G., Kao, T.C., Moise, T.S., Katz, A.J., Harton, T.B., and Woolsey, M., Real-time monitoring and control of resonant tunneling diode growth using spectroscopic ellipsometry, Semiconductor Characterization Present Status and Future Needs, 1996, pp. 507-511, American Institute of Physics, United States of America.

Bullis, W.M., Seiler, D.G., and Diebold, A.C. (editors), Collins, R.W., Lu, Y., Kim, S., and Wronski, C.R., Real time spectroellipsometry characterization of the fabrication of amorphous silicon solar cells, Semiconductor Characterization Present Status and Future Needs, 1996, pp. 517-521, American Institute of Physics, United States of America.

Bullis, W.M., Seiler, D.G., and Diebold, A.C. (editors), Gillmore III, W., Aspnes, D.E., and Lee, C.B., Performance capabilities of reflectometers and ellipsometers for compositional analysis during AlGaAs epitaxy, Semiconductor Characterization Present Status and Future Needs, 1996, pp. 522-526, American Institute of Physics, United States of America.

Bullis, W.M., Seiler, D.G., and Diebold, A.C. (editors), Pickering, C., Carline, R.T., Hope, D.A.O, and Robbins, D.J., In-situ monitoring of heteroepitaxial growth processes using real-time spectroscopic ellipsometry and laser light scattering, Semiconductor Characterization Present Status and Future Needs, 1996, pp. 532-536, American Institute of Physics, United States of America.

Bullis, W.M., Seiler, D.G., and Diebold, A.C. (editors), Solomon, P.R., Liu, S., Rosenthal, P.A., and Farquharson, S., Real-time measurement of film thickness, composition, and temperature by FT-IR emission and reflection spectroscopy, Semiconductor Characterization Present Status and Future Needs, 1996, pp. 544-548, American Institute of Physics, United States of America.

Yoshizawa, T. and Yokota, H (editors), Yamamoto, M., Mayama, K., Kimura, H., Furudate, M., and Yanagihara, M., The first thin film ellipsometry at a photon energy of 93eV with use of high performance multilayer polarizers, International Symposium on Polarization Analysis and Applications to Device Technology, 1996, pp. 70-73, vol. 2873, SPIE-The International Society for Optical Engineering, United States of America.

Yoshizawa, T. and Yokota, H (editors), Woollam, J.A., Gao, X., Heckens, S., and Hilfiker, J.N., In-situ monitor and control using fast spectroscopic ellipsometry, International Symposium on Polarization Analysis and Applications to Device Technology, 1996, pp. 140-143, vol. 2873, SPIE-The International Society for Optical Engineering, United States of America.

Yoshizawa, T. and Yokota, H (editors), Krishnan, S. and Nordine, P.C., Fast ellipsometry and Mueller-matrix ellipsometry using the division-of-amplitude photopolarimeter, International Symposium on Polarization Analysis and Applications to Device Technology, 1996, pp. 152-156, vol. 2873, SPIE-The International Society for Optical Engineering, United States of America.

Yoshizawa, T. and Yokota, H (editors), Shibuya, T., Amano, N., Kawabata, S., and Yokota, H., In-situ ellipsometric study of the growth of Au thin films, International Symposium on Polarization Analysis and Applications to Device Technology, 1996, pp. 168-171, vol. 2873, SPIE-The International Society for Optical Engineering, United States of America.

Yoshizawa, T. and Yokota, H (editors), Holzapfel, W, Neuschaefer-Rube, U., and Doberitzsch, J., Ellipsometric topometry for technical surfaces, International Symposium on Polarization Analysis and Applications to Device Technology, 1996, pp. 172-175, vol. 2873, SPIE-The International Society for Optical Engineering, United States of America.

Yoshizawa, T. and Yokota, H (editors), Holzapfel, W, Neuschaefer-Rube, U., and Neuschaefer-Rube, S., The photoelastic microellipsometer-a new tool for high-resolution force vector measurements, International Symposium on Polarization Analysis and Applications to Device Technology, 1996, pp. 176-179, vol. 2873, SPIE-The International Society for Optical Engineering, United States of America.

Yoshizawa, T. and Yokota, H (editors), Kitajima, M., Kamioka, I., Kurashina, T., and Nakamura, K.G., Initial plasma oxidation of silicon studied by real-time ellipsometry, International Symposium on Polarization Analysis and Applications to Device Technology, 1996, pp. 246-249, vol. 2873, SPIE-The International Society for Optical Engineering, United States of America.

Yoshizawa, T. and Yokota, H (editors), Kawabata, S., Miyanishi, Y., Ogawa, T., and Wakaki, M., In-situ ellipsometric study of phenomenon of photodoping of Ag metal into a-AsS film, International Symposium on Polarization Analysis and Applications to Device Technology, 1996, pp. 274-277, vol. 2873, SPIE-The International Society for Optical Engineering, United States of America.

Yoshizawa, T. and Yokota, H (editors), Yamaguchi, T., Jayatissa, A.H., Tonooka, S., Aoyama, M., Tabe, M., and Kanda, Y., Spectroellipsometric characterization of SIMOX with a very thin Si layer, International Symposium on Polarization Analysis and Applications to Device Technology, 1996, pp. 278-281, vol. 2873, SPIE-The International Society for Optical Engineering, United States of America.

Yoshizawa, T. and Yokota, H (editors), Yamaguchi, T., Ohshimo, K., Jayatissa, A.H., Aoyama, M., Gong, X.Y., Makino, T., and Kan, T., Spectroellipsometric study of sulphur passivation of InAs, International Symposium on Polarization Analysis and Applications to Device Technology, 1996, pp. 282-285, vol. 2873, SPIE-The International Society for Optical Engineering, United States of America.

Yoshizawa, T. and Yokota, H (editors), Boher, P., Stehle, J.L., Suzuki, Y., and Iwasaki, A., Characterization of laser annealed polysilicon by spectroscopic ellipsometry and comparison to other techniques, International Symposium on Polarization Analysis and Applications to Device Technology, 1996, pp. 294-296, vol. 2873, SPIE-The International Society for Optical Engineering, United States of America.

Yoshizawa, T. and Yokota, H (editors), Boher, P., Defranoux, C., Piel, J.P., Stehle, J.L., and Suzuki, Y., Fine characterization of ITO layers by spectroscopic ellipsometry, International Symposium on Polarization Analysis and Applications to Device Technology, 1996, pp. 297-300, vol. 2873, SPIE-The International Society for Optical Engineering, United States of America.

Yoshizawa, T. and Yokota, H (editors), Krishnan, S., Yugawa, K.J., and Nordine, P.C., Optical properties of liquid metals studied by spectroscopic ellipsometry, International Symposium on Polarization Analysis and Applications to Device Technology, 1996, pp. 314-315, vol. 2873, SPIE-The International Society for Optical Engineering, United States of America.

Tompkins, H.G. and McGahan, W.A., Spectroscopic Ellipsometry and Reflectometry, 1999, pp. 75-130 and 166-180 and 195-198, John Wiley & Sons, Inc., United States of America.

Zettler, J.T., Characterization of epitaxial semiconductor growth by reflectance anisotropy spectroscopy and ellipsometry, Prog. Crystal Growth and Charact., 1997, pp. 27-98, vol. 35, Elsevier Science, Ltd., Great Britain.

Adachi, Sadao., Optical Constants of Crystalline and Amorphous Semiconductors, 1999, pp. 1-18, Kluwer Academic Publishers, United States of America.

Adachi, Sadao., Optical Properties of Crystalline and Amorphous Semiconductors, 1999, pp. 120-129, Kluwer Academic Publishers, United States of America.

Cigal, Jean-Charles., A Novel Spectroscopic Ellipsometer in the Infrared, 2002, pp. 1-70, Universiteitsdrukkerij Technische Universiteit Eindhoven, Germany.

Kasic, A., Phonons, free-carrier properties, and electronic interband transitions of binary, ternary, and quaternary group-III nitride layers measured by spectroscopic ellipsometry, 2003, pp. 17-26, Shaker Verlag GmbH, Germany.

Tompkins, H.G., A User's Guide to Ellipsometry, 1993, pp. 35-81 and 109-134 and 196-216 and 246-252, Academic Press, Inc., United States of America.

* cited by examiner

| 1 | cauchy | 400 Å |
|---|--------|-------|
| 0 | si_vuv | 1 mm |

| 1 | genosc | 400 Å |
|---|--------|-------|
| 0 | si_vuv | 1 mm |

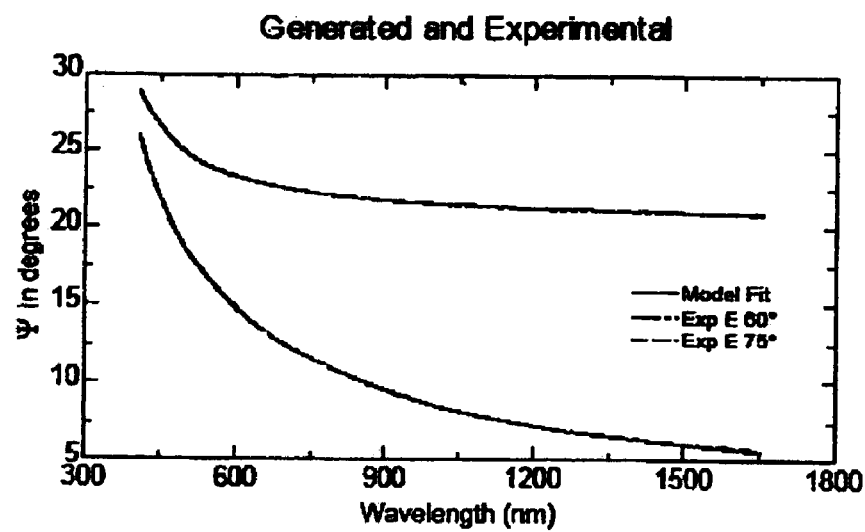
FIG. 7d
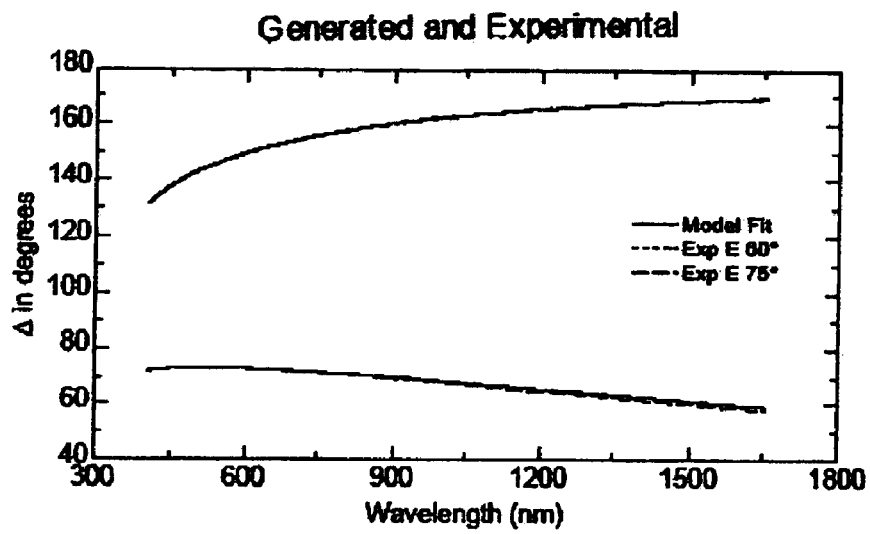
FIG. 7e
| 1 | cauchy | 224.39 Å |
|---|--------|----------|
| 0 | si_vuv | 1 mm |
FIG. 7f

SAMPLE ANALYSIS METHODOLOGY UTILIZING ELECTROMAGNETIC RADIATION

This Application is a CIP of application Ser. No. 10/713,816 Filed Nov. 17, 2003 and Ser. No. 10/376,677 Filed Feb. 28, 2003 now U.S. Pat. No. 6,982,792; and Claims Benefit of Provisional Applications Ser. Nos. 60/471,769 Filed May 20, 2003, and 60/485,009 Filed Jul. 5, 2003, and 60/527,553 Filed Dec. 6, 2003.

TECHNICAL FIELD

The disclosed invention relates to methodology for analysis of sample systems utilizing electromagnetic radiation; and more particularly to the simultaneous use of wavelengths in at least two ranges selected from RADIO, MICRO, FIR, IR, NIR-VIS-NUV, UV, DUV, VUV, EUV and XRAY in a regression procedure to evaluate parameters in mathematical dispersion relationships.

BACKGROUND

It is well known to apply electromagnetic radiation to evaluate optical properties of sample systems. The disclosed invention can comprise any means for generating an electromagnetic beam and causing it to impinge upon a sample system, such as:
reflectometer;
spectrophotometer;
ellipsometer;
spectroscopic ellipsometer;
polarimeter; and
spectroscopic polarimeter;
with reflected or transmitted electromagnetic radiation being directed to enter a detector.

For breadth it is noted that while semiconductor sample systems with one or more thin film on their surface are typical of those to which ellipsometry can be applied, essentially any sample can be subjected to investigation using electromagnetic radiation. Non-limiting Examples are amples which comprise:
Materials with High or Low Extinction Coefficient (K);
Materials with High or Low Refractive Index (N);
Metals;
Semimetals;
Semiconductors;
Insulators;
Transparent Oxides;
Liquids;
Fluids;
oils;
Lubricants;
Biological materials;
Nucleic Acids;
DNA &/or RNA;
Proteins;
Amino Acids;
Carbohydrates;
Waxes;
Fats;
Lipids;
Plant material;
Animal material;
Fungi material;
Microbe material;
Tissues;
Condensates;
Combination Solid and Liquid &/or Gas sample systems;
Liquid Crystals;
free standing films;
Porous materials;
Alloys;
Compounds;
Composites;
Ceramics;
Polymers;
Fiberous materials;
Wood containing materials;
Paper containing materials;
Plastics;
Crystaline materials;
Amorphous materials;
Polycrystaline Materials;
Glassy materials;
Homogeneous materials;
Inhomogeneous materials;
Superlattices;
Superconductors;
Lamgmuir-Blodgett materials;
Monolayers;
Fractional Monolayers;
Multi layers;
Samples comprising Quantum Dots &/or Wells;
Polymers;
Conjugated Polymers;
Films of any material on substrate of another material;
Monoparticles;
Composites containing monoparticles;
Nanomaterials;
Materials containing Nanomaterials;
Superlattices with Nanoparticles;
combinations of the above.

It is further noted that many types of ellipsometer systems exist. Examples are Nulling, Rotating Polarizer, Rotating Analyzer, Rotating Compensator, Modulation Element etc. but all have in common that they provide data which allow determination of PSI ($\Psi$) and DELTA ($\Delta$) of a Sample, where ($\Psi$) and ($\Delta$) are defined by:

$$\rho = rp/rs = \mathrm{Tan}(\Psi) \exp(i\Delta)$$

Tan ($\Psi$) or Cos ($\Delta$), coordinates on a Poincare Sphere or other descriptors of the Polarization State of electromagnetic radiation are to be understood as equivalents to PSI ($\Psi$) and DELTA ($\Delta$), as are the Coefficients "IN" "S" & "C":

$$N = \mathrm{Cos}(2\Psi);$$

$$C = \mathrm{Sin}(2\Psi)\mathrm{Cos}(\Delta);$$

$$S = \mathrm{Sin}(2\Psi)\mathrm{Sin}(\Delta);$$

in Modulation Ellipsometers, (see U.S. Pat. Nos. 5,416,588 and 5,956,145 which are incorporated by reference hereinto).

Further, evaluation can be achieved for at least one sample system characterizing selection from the group consisting:
energy gap;
index of refraction;
growth rate;
etch rate;
thickness;

extinction coefficient;
carrier concentration;
alloy ratio;
critical point;
depolarization rate;
inhomogenuity;
grading;
anisotropy;
temperature;
crystalinity;
stress;
strain;
surface layer roughness;
interface layer;
interface roughness;
electro-optic coefficient;
magneto-optic coefficient;
chemical bond presence;
chemical bond strength;
sample system phase;
combinations of the above.

It is also noted that data can be obtained which is characterized by at least one selection from the group consisting of:
reflected electromagnetic radiation;
transmitted electromagnetic radiation;
single sample system invesitgated;
multiple sample systems simultaneously
investigated;
single angle of incidence of electromagnetic
radiation;
single sample system orientation;
multiple sample system orientations;
multiple angles of incidence of
electromagnetic radiation;
date acquired from single instrument;
data acquired from multiple instruments;
focused beam of electromagnetic radiation;
divergent beam of electromagnetic radiation;
unfocused beam of electromagnetic radiation;
in-situ;
ex-situ;
electro-optic;
electro-opticcoincident with ellipsometric data;
kerr magneto-optic;
kerr magneto-optic coincident with ellipsometric data;
combinations of the above.

Briefly, methodology provides that electromagnetic radiation be caused to interact with a sample system, with detected changes in intensity and/or polarization state being used to evaluate the sample system optical constants. Spectrophotometry and Reflectometry detect changes in Intensity of a beam of electromagnetic radiation resulting from interaction with a sample system. Ellipsometry characterizes change in polarization state caused by interaction of a beam of electromagnetic radiation with a sample system. And while strong correlation typically exists between thin film thickness and optical constants, Ellipsometric data can, at times, be sufficient to evaluate the thickness of a thin flim on a sample system and its refractive index and extinction coeficient, (or the mathematically equivalent real and imaginary parts of the dielectric function). Combined with Spectrophotometry and Reflectometry data serves to to enable less correlated determination of sample system properties.

Further, while use of data at a single wavelength can provide beneficial results in many situations, it is typical to obtain data at a multiplicity of wavelengths, and perhaps at a plurality of Angles of Incidence (AOI) at which a beam of electromagnetic radiation is caused to approach a sample system. This allows determining the refractive index and extinction coeficient or the mathematically equivalent real and imaginary parts of the dielectric function over a spectroscopic range.

Continuing, it is known to:
provide a sample system and obtain characterizing data therefrom comprising change in spectroscopic electromagnetic radiation caused to interact therewith, said change being caused by said interaction, and
provide a mathematical model of the sample system; and
perform a regression procudure of the mathematical model onto the data to evaluate parameters in the mathematical model.

Where data is to be obtained in two different wavelength ranges, possible non-limiting combination of instruments which operate in said different spectral ranges are:
Two Ellipsometer Systems operating in different wavelength ranges;
One Ellipsometer and a Transmission Spectrometer;
One Ellipsometer and a Reflection Spectrometer;
Two Spectrometer Systems, one Reflection mode and one Transmission mode.

Again, where ellipsometry is applied the change is in polarization state, rather than intensity of the spectroscopic electromagnetic radiation caused by reflection from or transmission through the sample system.

By said known methodology insight to the composition and optical properties of the sample system can be determined.

Typically the spectroscopic electromagnetic radiation is obtained using an instrument which provides wavelengths in a range selected from the group:
Radio;
Micro
Far Infrared (FIR);
Infrared (IR);
NIR-VIS-NUV;
Near Infrared (NIR);
Visual (VIS);
Near Ultraviolet (NUV);
Ultraviolet (UV);
Deep Ultraviolet (DUV);
Vacuum Ultraviolet (VUV);
Extreme Ultraviolet (EUV);
X-Ray (XRAY);

and while wavelengths from one said selection is often sufficient to provide good evaluation of parameters in a mathematical model of a sample system, it does occur that some parameters in a mathematical model can not be investigated by wavelengths in a single selected range of wavelengths. For instance, wavelengths in the IR range are typically appropriate for investigation of the nature of chemical bonds in molecularly bonded sample systems, and IR, NIR, VIS and UV wavelengths are all suited to obtaining information about absorption and electron transitions in numerous material, (eg. semiconductors, semi-metals and metals). NIR wavelengths are particularly applicable to investigtion of semi-metals and VIS wavelengths to metals. Another example is that the angle of incidence of an IR beam with respect to a normal to a surface of a sample system is often strongly correlated with the absolute index of refraction of the sample system, but UV-VIS-NIR wavelengths are often capable of accurately evaluating the index and its dispersion, thereby enabling breaking of said correlation.

The following provides insight to various Sample System Physical Parameters and Spectral Ranges typically utilized to provide insight thereto:

| PHYSICAL PARAMETER | SPECTRAL RANGE |
|---|---|
| PHONON ABSORPTION | MID-IR (MIR) TO FAR-IR (FIR) |
| MOLECULAR BOND ABSORPTION CHEMISTRY INFORMATION) | MIR TO FIR |
| FREE CARRIER ABSORPTION IN METALS | UV-VIS AND LONGER WAVELENGTHS |
| FREE CARRIER ABSORPTION IN CONDUCTIVE OXIDES | NEAR-IR (NIR) |
| FREE CARRIER ABSORPTION IN SEMICONDUCTORS | MIR TO FIR |
| SURFACE ROUGHNESS | UV-VIS (THOUGH DIFFERENT WAVELENGTH RANGES GIVE INFORMATION ON DIFFERENT LEVELS OF ROUGHNSS) |
| SMALL SCALE INDEX GRADING | ABSORBING REGIONS IN VACUUM ULTRA VIOLET (VUV) TO NIR |
| LARGE SCALE INDEX GRADING | ANY SPECTRAL REGION |
| THICKNESS NON-UNIFORMITY | ANY SPECTRAL ALTHOUGH RANGE SENSITIVITY INCREASES AT SHORTER WAVELENGTHS |
| ANISOTROPY | ANY SPECTRAL RANGE - VARIES WITH SAMPLE |
| DICHROISM | ABSORBING REGION-TYPICALLY UV OR IR |
| ABSORPTION DUE TO ELECTRONIC TRANSITIONS | UV TO VIS AND NIR - NIR WITH NARROW BANDGAP SEMICONDUCTORS |
| ALLOY RATIOS | UV-VIS |
| NATIVE OXIDES (SEMICONDUCTORS) | UV-VIS |
| ULTRA-THIN FILM THICKNESS | UV |
| OXYGEN IN LIVING TISSUES & WATER IN VARIOUS STATES & BIOLOGICAL MATTER | VIS RED-NIR |

It is also noted that published Optical Constant data for many materials, (eg gold), even today often have discontinuous steps or jumps therein which result from the use of different investigating systems on either-side of the discontinuity. That is, the Optical Constants arrived at using data obtained from an Ellipsometer capable in the IR wavelength range, and Optical Constants arrived at using data obtained from an Ellipsometer capable in the NIR-VIS waelength range are often not continuous at the interface wavelengths. The discontinuity is, of course, an artifact.

In view of the above it should be apparant that simultaneous use of information gathered from various wavelength ranges from the same or different investigation systems in a single regression procudure, would enable the ability to better evaluate sample systems and provide more realistic results.

While it is often the practice to regress on a point by point, (ie. wavelength by wavelength), basis in wavelength regions where a sample system is opague, regression based evaluation of parameters in a mathematical model preferably involves parameterization in wavelength regions where a sample system, (eg. a bulk material and substrates with layers thereupon), is transparent and where reflected electromagnetic radiation demonstrates minimal absorption and typically interference efects resulting from reflections from interfaces between layers as well as from the surface. Parameterization can provide Kramers- Kronig consistency, resulting in physical optical constants, and often reduces the number of parameters that are required to be evaluated to accurately model very irregular data. Parameterization also avoids discontinuities and reduces the effects of noise in optical constants by modeling with smooth mathematical functions. Disclosed in the J.A. Woollam Co. W-VASE32 (Registered Trademark), Manual are various approaches, including the mathematics thereof, to Parameterization, including:

Cauchy;
    Cauchy +Urbach absorption;
    Sellmeier Oscillator, (zero broadened);
    Lorentz Oscillator;
    Gaussian Oscillator;
    Harmonic Oscillator;
    Drude Oscillator;
    Tauc-Lorentz Oscillator;
    Cody-Lorentz Oscillator;
    Tanguay;
    Ionic Oscillator;
    TOLO;
    Gauss-Lorentz Oscillator;
    Gauss-Lorentz Oscillator Asymetric Doublet (GLAD) Oscillator;
    Herzinger-Johs Parametric Semiconductor Oscillator Model;
    Psemi-Eo Oscillator;
    Critical Point Parabolic band (CPPB);
    Adachi Oscillator Model;
    Pole;

wherein the Oscillators are preferably Kramers-Kronig consistent.

Following directly are mathematical descriptions of many of the foregoing Oscillator Structures, which are presently available in the J.A. Woollam Co. WVASE32 (Registered Trademark), GEMOSC™ Layer. Said GEMOSC™ layer can be invoked once Dielectric Function plots are known over a Spectroscopic Range by other means, and enables placing Oscillator Strurctures of appropriate shape at appropriate locations under, for instance, the imaginary part of said Dielectric Function such that summation of their contributions at each wavelength results in said Dielectric Function. The oscillator Structures are Kramers-Kronig consistant, hence modeling the Imaginary part allows calculation of the real part.

e1 Offset:
Purely real constant added to $\epsilon 1$. It is equivalent to "$\epsilon co$", which is often seen in scientific literature.

Sellmeier:

| Style | Equation | Fit Parameters |
|---|---|---|
| Sell.0 (nm) Sell.5 (μm) | $\varepsilon_{n\_sellmeier} = \dfrac{A_n \cdot \lambda^2 \lambda_n^2}{\lambda^2 - \lambda_n^2}$ | Ampn = $A_n$ (nm$^{-2}$), Wvln = $\lambda_n$ (nm) Ampn = $A_n$ (μm$^{-2}$), Wvln = $\lambda_n$ (μm) |
| Sell.1 (nm) Sell.6 (μm) | $\varepsilon_{n\_sellmeier} = \dfrac{A_n \cdot \lambda^2 \lambda_n}{\lambda^2 - \lambda_n^2}$ | Ampn = $A_n$ (nm$^{-1}$), Wvln = $\lambda_n$ (nm) Ampn = $A_n$ (μm$^{-1}$), Wvln = $\lambda_n$ (μm) |
| Sell.2 (nm) Sell.7 (μm) | $\varepsilon_{n\_sellmeier} = \dfrac{A_n \cdot \lambda^2}{\lambda^2 - \lambda_n^2}$ | Ampn = $A_n$ (dimensionless), Wvln = $\lambda_n$ (nm) or Wvln = $\lambda_n$ (μm) n = 1, 2 |

Cauchy:

| Style | Equation | Fit Parameters |
|---|---|---|
| Chy.0 | $N_n = A_n + \dfrac{B_n}{\lambda^2} + \dfrac{C_n}{\lambda^4}$ | Ann = $A_n$, Bnn = $B_n$, Cnn = $C_n$, (dimensionless) $\lambda$ (μm) |
|  | $K_n = \alpha e^{\beta\left(1.24\left(\frac{1}{\lambda} - \frac{1}{\gamma}\right)\right)}$ | Akn = $\alpha$ (dimensionless) Bkn = $\beta$ (μm$^{-1}$), |
|  | $\varepsilon_{n\_Cauchy} = (N_n + iK_n)^2$ | Ckn = $\gamma$ (μm) (user adjustable but not fittable. Only valid when $\lambda > \gamma$) |

Drude

| Style | Equation | Fit Parameters |
|---|---|---|
| Drd.0 (eV) Drd.5 (cm$^{-1}$) | $\varepsilon_{n\_Drd} = -\dfrac{A_n Br_n}{E^2 + iBr_n E}$ | Ampn = $A_n$ (eV) Brn = $Br_n$ (eV) Ampn = $A_n$ (cm$^{-1}$), Brn = $Br_n$ (cm$^{-1}$) |
| Drd.1 (eV) Drd.6 (cm$^{-1}$) | $\varepsilon_{n\_Drd} = -\dfrac{A_n}{E^2 + iBr_n E}$ | Ampn = $A_n$ (eV$^2$), Brn = $Br_n$ (eV) Ampn = $A_n$ (cm$^{-2}$), Brn − $Br_n$ (cm$^{-1}$) | rho-tau Drude & N-mu Drude:

| Style | Equation | Fit Parameters | Calculated Parameters (mstar known) |
|---|---|---|---|
| Rho-tau.0 | $\varepsilon_{n\_rtDrd} = \dfrac{-\hbar^2}{\varepsilon_0 \rho_n (\tau_n \cdot E^2 + i\hbar E)}$ | rhon = $\rho_n$ (Ω-cm), taun = $\tau_n$ ($10^{-15}$ sec) | |
| Rho-tau.5 | $\rho_n = \dfrac{m^*}{N_n q^2 \tau_n} = \dfrac{1}{q\mu_n N_n}$ | rhon = $\log_{10}(\rho_n)$ (Ω-cm), taun = $\tau_n$ ($10^{-15}$ sec) | $\log_{10}(N)$ (cm$^{-3}$) $\mu$ (cm$^2$V$^{-1}$ sec$^{-1}$) |
| N-mu.0 | $\varepsilon_{n\_N\mu Drd} = \dfrac{-\hbar^2}{\varepsilon_0 \rho_n (\tau_n \cdot E^2 + i\hbar E)}$ | Nn = $N_n$ (cm$^{-3}$), mun = $\mu_n$ (cm$^2$V$^{-1}$ sec$^{-1}$) | N (cm$^{-3}$), $\mu$ (cm$^2$V$^{-1}$ sec$^{-1}$) |
| N-mu.5 | $\rho_n = \dfrac{m^*}{Nq^2\tau} = \dfrac{1}{q\mu N}$ | Rhon − $\log_{10}(N_n)$ (Ω-cm) taun = $\tau_n$ ($10^{-15}$ sec) | $\log_{10}(N)$ (cm$^{-3}$) $\mu$ (cm$^2$V$^{-1}$ sec$^{-1}$) |

-continued e1 Offset:
Purely real constant added to $\epsilon 1$. It is equivalent to "$\epsilon\infty$",
which is often seen in scientific literature.

Lorentz:

| Style | Equation | Fit Parameters |
|---|---|---|
| Lor.0 (eV) <br> Lor.5 (cm$^{-1}$) | $\varepsilon_{n\_Lorentz} = \dfrac{A_n Br_n E_n}{E_n^2 - E^2 - iBr_n E}$ | Ampn = $A_n$ (dimensionless), <br> Enn = $E_n$ (eV), Brn = $Br_n$ (eV) <br> Ampn = $A_n$ (dimensionless), <br> En1 = $E_n$ (cm$^{-1}$), Br1 = $Br_n$ (cm$^{-1}$) |
| Lor.1 (eV) <br> Lor.6 (cm$^{-1}$) | $\varepsilon_{n\_Lorentz} = \dfrac{A_n E_n}{E_n^2 - E^2 - iBr_n E}$ | Ampn = $A_n$ (eV), <br> Enn = $E_n$ (eV), Brn = $Br_n$ (eV) <br> Ampn = $A_n$ (cm$^{-1}$), <br> Enn = $E_n$ (cm$^{-1}$), Brn = $Br_n$ (cm$^{-1}$) |
| Lor.2 (eV) <br> Lor.7 (cm$^{-1}$) | $\varepsilon_{n\_Lorentz} = \dfrac{A_n E_n^2}{E_n^2 - E^2 - iBr_n E}$ | Ampn = $A_n$ (dimensionless), <br> Enn = $E_n$ (eV), Brn = $Br_n$ (eV) <br> Ampn = $A_n$ (dimensionless), <br> Enn = $E_n$ (cm$^{-1}$), Brn = $Br_n$ (cm$^{-1}$) |

Harmonic

| Style | Equation | Fit Parameters |
|---|---|---|
| Lor.0 (eV) <br> Lor.5 (cm$^{-1}$) | $\varepsilon_{n\_Harmonic} = \dfrac{A_n Br_n E_n}{E_n^2 - E^2 + 1/4 Br_n^2 - iBr_n E}$ | Ampn = $A_n$ (dimensionless), <br> Enn = $E_n$ (eV), Brn = $Br_n$ (eV) <br> Ampn = $A_n$ (dimensionless), <br> En1 = $E_n$ (cm$^{-1}$), Br1 = $Br_n$ (cm$^{-1}$) |
| Lor.1 (eV) <br> Lor.6 (cm$^{-1}$) | $\varepsilon_{n\_Harmonic} = \dfrac{A_n E_n}{E_n^2 - E^2 + 1/4 Br_n^2 - iBr_n E}$ | Ampn = $A_n$ (eV), <br> Enn = $E_n$ (eV), Brn = $Br_n$ (eV) <br> Ampn = $A_n$ (cm$^{-1}$), <br> Enn – $E_n$ (cm$^{-1}$), Brn = $Br_n$ (cm$^{-1}$) |
| Lor.2 (eV) <br> Lor.7 (cm$^{-1}$) | $\varepsilon_{n\_Harmonic} = \dfrac{A_n E_n^2}{E_n^2 - E^2 + 1/4 Br_n^2 - iBr_n E}$ | Ampn = $A_n$ (dimensionless), <br> Enn = $E_n$ (eV), Brn = $Br_n$ (eV) <br> Ampn = $A_n$ (dimensionless), <br> Enn = $E_n$ (cm$^{-1}$), Brn = $Br_n$ (cm$^{-1}$) |

Gaussian:

| Style | Equation | Fit Parameters |
|---|---|---|
| | $\varepsilon_{n\_Gaussian} = \varepsilon_{n1} + i\varepsilon_{n2}$, where <br> $\varepsilon_{n1} = \dfrac{2}{\pi} P \displaystyle\int_{R_g}^{\infty} \dfrac{\xi \varepsilon_{n2}(\xi)}{\xi^2 - E^2} d\xi$, <br> using $\varepsilon_{n2}$ as defined below. | |
| Gau.0 (eV) <br> Gau.5 (cm$^{-1}$) | $\varepsilon_{n2} = A_n e^{-\left(\frac{E-E_n}{Br_n}\right)^2} + A_n e^{-\left(\frac{E+E_n}{Br_n}\right)^2}$ | Ampn = $A_n$ (dimensionless), <br> Enn = $E_n$ (eV), Brn = $Br_n$ (eV) <br> Ampn = $A_n$ (dimensionless), <br> En1 = $E_n$ (cm$^{-1}$), Br1 = $Br_n$ (cm$^{-1}$) |
| Gau.1 (eV) <br> Gau.6 (cm$^{-1}$) | $\varepsilon_{n2} = \dfrac{A_n}{Br_n} e^{-\left(\frac{E-E_n}{Br_n}\right)^2} + \dfrac{A_n}{Br_n} e^{-\left(\frac{E+E_n}{Br_n}\right)^2}$ | Ampn = $A_n$ (eV), <br> Enn = $E_n$ (eV), Brn = $Br_n$ (eV) <br> Ampn = $A_n$ (cm$^{-1}$), <br> Enn = $E_n$ (cm$^{-1}$), Brn = $Br_n$ (cm$^{-1}$) |
| Gau.2 (eV) <br> Gau.7 (cm$^{-1}$) | $\varepsilon_{n2} = \dfrac{A_n E_n}{Br_n} e^{-\left(\frac{E-E_n}{Br_n}\right)^2} + \dfrac{A_n E_n}{Br_n} e^{-\left(\frac{E+E_n}{Br_n}\right)^2}$ | Ampn = $A_n$ (dimensionless), <br> Enn = $E_n$ (eV), Brn = $Br_n$ (eV) <br> Ampn = $A_n$ (dimensionless), <br> Enn = $E_n$ (cm$^{-1}$), Brn = $Br_n$ (cm$^{-1}$) |

-continued e1 Offset:
Purely real constant added to $\epsilon 1$. It is equivalent to "$\epsilon\text{co}$", which is often seen in scientific literature.

---

Gauss-Lorentz:

$$\varepsilon_n = i\Phi_n\left[\int_0^\infty e^{i(\hbar\omega - E_n + iBr_n\gamma_n(s))s}ds + \int_0^\infty e^{i(\hbar\omega + E_n + iBr_n\gamma_n(s))s}ds\right],$$

where $\gamma_n(s) = \Gamma_n + 2\sigma_n^2 s$, $e^{Bmix_n} = \dfrac{\Gamma_n}{\sigma_n}$, and $\Phi$ is defined below.

| Style | $\Phi$ | Fit Parameters | Calculated Parameters |
|---|---|---|---|
| G-L.0 (eV) | $\Phi = A_n$ | $A_n$ = Ampn (dimensionless), $E_n$ = Enn (eV), $Br_n$ = Brn (eV), $Bmix_n$ = Bmixn (dimensionless) | $\Gamma_n$ = Blorn (eV), $\sigma_n$ = Bgaussn (eV) |
| G-L.5 (cm$^{-1}$) | | $A_n$ = Ampn (dimensionless), $E_n$ = Enn (cm$^{-1}$), $Br_n$ = Brn (cm$^{-1}$), $Bmix_n$ = Bmixn (dimensionless) | $\Gamma_n$ = Blorn (cm$^{-1}$), $\sigma_n$ = Bgaussn (cm$^{-1}$) |
| G-L.1 (eV) | $\Phi = \dfrac{A_n}{Br_{nn}}$ | $A_n$ = Ampn (eV), $E_n$ = Enn (eV), $Br_n$ = Brn (eV), $Bmix_n$ = Bmixn (dimensionless) | $\Gamma_n$ = Blorn (eV), $\sigma_n$ = bgaussn (eV) |
| G-L.6 (cm$^{-1}$) | | $A_n$ = Ampn (cm$^{-1}$), $E_n$ = Enn (cm$^{-1}$), $Br_n$ = Brn (cm$^{-1}$), $Bmix_n$ = Bmixn (dimensionless) | $\Gamma_n$ = Blorn (cm$^{-1}$), $\sigma_n$ = Bgaussn (cm$^{-1}$) |
| G-L.2 (eV) | $\Phi = \dfrac{A_n E_n}{Br_{nn}}$ | $A_n$ = Ampn (eV), $E_n$ = Enn (eV), $Br_n$ = Brn (eV), $Bmix_n$ = Bmixn (dimensionless) | $\Gamma_n$ = Blorn (eV), $\sigma_n$ = bgaussn (eV) |
| G-L.7 (cm$^{-1}$) | | $A_n$ = Ampn (cm$^{-1}$), $E_n$ = Enn (cm$^{-1}$), $Br_n$ = Brn (cm$^{-1}$), $Bmix_n$ = Bmixn (dimensionless) | $\Gamma_n$ = Blorn (cm$^{-1}$), $\sigma_n$ = Bgaussn (cm$^{-1}$) |

---

Tauc-Lorentz & Egap Tauc-Lorentz:

| Style | Equation | Fit Parameters |
|---|---|---|
| T-L.0 (eV) | $\varepsilon_{n\_T-L} = \varepsilon_{n1} + i\varepsilon_{n2}$, where | Ampn = $A_n$ (dimensionless), Enn = $Eo_n$ (eV), Cn = $C_n$ (eV), Egn = $Eg_n$ (eV) |
| EgT-L.o (eV) | $\varepsilon_{n2} = \dfrac{A_n(E - Eg_n)^2}{(E^2 - Eo_n^2) + C_n^2} \dfrac{\Theta(E - Eg_n)}{E}$ and $\varepsilon_{n1} = \dfrac{2}{\pi}P\int_{R_g}^\infty \dfrac{\xi\varepsilon_{n2}(\xi)}{\xi^2 - E^2}d\xi *$ | Egap T-L.0: same as above, except Egap = Eg (eV) |

---

Ionic1 & Ionic2:

| Style | Equation | Fit Parameters |
|---|---|---|
| Ion1.0 (eV) | $\varepsilon_{n\_Ion1} = \varepsilon_{\infty n} + \dfrac{E_{Tn}^2(\varepsilon_{dcn} - \varepsilon_{\infty n})}{E_{Tn}^2 - E^2 - iBr_n E}$ | edcn = $\epsilon_{dcn}$ (dimensionless), einfn = $\epsilon_{\infty n}$ (dimensionless), Eton = $E_{Tn}$ (eV), Brn = $Br_n$ (eV) |
| Ion1.5 (cm$^{-1}$) | | edcn = $\epsilon_{dcn}$ (dimensionless), einfn = $\epsilon_{\infty n}$ (dimensionless), Eton = $E_{Tn}$ (cm$^{-1}$), Brn = $Br_n$ (cm$^{-1}$) |
| Ion2.0 (cV) | $\varepsilon_{n\_Ion1} = \varepsilon_{dcn}\left(\dfrac{E_{Tn}^2}{E_{Ln}^2} + \dfrac{E_{Tn}^2\left(1 - \dfrac{E_{Tn}^2}{E_{Ln}^2}\right)}{E_{Tn}^2 - E^2 - iBr_n E}\right)$ | edcn = $\epsilon_{dcn}$ (dimensionless), eton = $E_{Tn}$ (eV), Brn = $Br_n$ (eV), Elon = $E_{L,n}$ (eV) |
| Ion2.5 (cm$^{-1}$) | | edcn = $\epsilon_{dcn}$ (dimensionless), Eton = $E_{Tn}$ (cm$^{-1}$), Brn = $Br_n$ (cm$^{-1}$), Elon = $E_{Ln}$ (eV) |

-continued e1 Offset:
Purely real constant added to ε1. It is equivalent to "εco",
which is often seen in scientific literature.

TOLO:

| Style | Equation | Fit Parameters |
|---|---|---|
| TOLO.0 (eV) | $\varepsilon_{n\_TOLO} = A_n \dfrac{E_{lon}^2 - E^2 - iB_{lon}E}{E_{ton}^2 - E^2 - iB_{ton}E}$ | Ampn = $A_n$ (dimensionless), Elon = $E_{lon}$ (eV), $E_{ton}$ = Eton (eV) Blon = $B_{lon}$ (eV), Bton = $B_{ton}$ (eV) |
| TOLO.5 (cm$^{-1}$) | | Ampn = $A_n$ (dimensionless), Elon = $E_{lon}$ (cm$^{-1}$), Eton = $E_{ton}$ (cm$^{-1}$) Blon = $B_{lon}$ (cm$^{-1}$), Bton = $B_{ton}$ (cm$^{-1}$) |
| TOLO.1 (eV) | $\varepsilon_{n\_TOLO} = \dfrac{A_n}{B_{ton}} \dfrac{E_{lon}^2 - E^2 - iB_{lon}E}{E_{ton}^2 - E^2 - iB_{ton}E}$ | Ampn = $A_n$ (eV), Elon = $E_{lon}$ (eV), $E_{ton}$ = Eton (eV) Blon = $B_{lon}$ (eV), Bton = $B_{ton}$ (eV) |
| TOLO.6 (cm$^{-1}$) | | Ampn = $A_n$ (cm$^{-1}$), Elon = $E_{lon}$ (cm$^{-1}$), Eton = $E_{ton}$ (cm$^{-1}$) Blon = $B_{ton}$ (cm$^{-1}$), Bton = $B_{ton}$ (cm$^{-1}$) |
| TOLO.2 (eV) | $\varepsilon_{n\_TOLO} = A_n \dfrac{E_{ton}}{B_{ton}} \dfrac{E_{lon}^2 - E^2 - iB_{lon}E}{E_{ton}^2 - E^2 - iB_{ton}E}$ | Ampn = $A_n$ (dimensionless), Elon = $E_{lon}$ (eV), Eton = Eton (eV) Blon = $B_{lon}$ (eV), Bton = $B_{ton}$ (eV) |
| TOLO.7 (cm$^{-1}$) | | Ampn = $A_n$ (dimensionless), Elon = $E_{lon}$ (cm$^{-1}$), Eton = $E_{ton}$ (cm$^{-1}$) Blon = $B_{lon}$ (cm$^{-1}$), Bton = $B_{ton}$ (cm$^{-1}$) |

GLAD:

Separation$_n$ = Split$_n$ × Br$_n$
Asym$_n$ > 0: (lower-energy peak) < (higher-energy peak)
Asym$_n$ < 0: (lower-energy peak) > (higher-energy peak)
Asym$_n$ = 0: (lower-energy peak) = (higher-energy peak)
The two peaks are Gauss-Lorentz oscillators and are defined as $$\varepsilon_n = i\Phi_n \left[ \int_0^\infty e^{i(\hbar\omega - E_n + iBr_n\gamma_n(s))s} ds + \int_0^\infty e^{i(\hbar\omega + E_n + iBr_n\gamma_n(s))s} ds \right],$$

where $\gamma_n(s) = \Gamma_n + 2\sigma_n^2 s$, $e^{Bmix_n} = \dfrac{\Gamma_n}{\sigma_n}$, and
Φ is defined below.

| Style | Φ | Fit Parameters |
|---|---|---|
| GLAD.0 (eV) | $\Phi = A_n$ | $A_n$ = Ampn (dimensionless), $E_n$ = Enn (eV), $Br_n$ = Brn (eV), Split$_n$ = Splitn, Asym$_n$ = Asymn, Bmix$_n$ = Bmixn (Splitn, Asymn, & Bmixn all dimensionless) |
| GLAD.5 (cm$^{-1}$) | | $A_n$ = Ampn (dimensionless), $E_n$ = Enn (cm$^{-1}$), $Br_n$ = Brn (cm$^{-1}$), Split$_n$ = Splitn, Asym$_n$ = Asymn, Bmix$_n$ = Bmixn (Splitn, Asymn, & Bmixn all dimensionless) |
| GLAD.1 (eV) | $\Phi = \dfrac{A_n}{Br_{nn}}$ | $A_n$ = Ampn (eV), $E_n$ = Enn (eV), $Br_n$ = Brn (eV) Split$_n$ = Splitn, Asym$_n$ = Asymn, Bmix$_n$ = Bmixn (Splitn, Asymn, & Bmixn all dimensionless) |
| GLAD.6 (cm$^{-1}$) | | $A_n$ = Ampn (cm$^{-1}$), $E_n$ = Enn (cm$^{-1}$), $Br_n$ = Brn (cm$^{-1}$) Split$_n$ = Splitn, Asym$_n$ = Asymn, Bmix$_n$ = Bmixn (Splitn, Asymn, & Bmixn all dimensionless) |
| GLAD.2 (eV) | $\Phi = \dfrac{A_n E_n}{Br_{nn}}$ | $A_n$ = Ampn (dimensionless), $E_n$ = Enn (eV), $Br_n$ = Brn (eV) Split$_n$ = Splitn, Asym$_n$ = –Asymn, Bmix$_n$ = Bmixn (Splitn, Asymn, & Bmixn all dimensionless) |
| GLAD.7 (cm$^{-1}$) | | $A_n$ = Ampn (dimensionless), $E_n$ = Enn (cm$^{-1}$), $Br_n$ = Brn (cm$^{-1}$) Split$_n$ = Splitn, Asym$_n$ = Bmix$_n$ = Bmixn (Splitn, Asymn, & Bmixn all dimensionless) |

-continued e1 Offset:
Purely real constant added to ε1. It is equivalent to "εco",
which is often seen in scientific literature.

CPPB:

$$\varepsilon_n = \Phi e^{i\theta_n}\left(\frac{\Gamma}{2E_{gn} - 2E - i\Gamma_n}\right)^{\mu_n}, \mu_n = \pm 1/2$$

$$\varepsilon_n = \Phi e^{i\theta_n} \ln(2E_{gn} - 2E - i\Gamma_n), \text{ for } \mu_n = 0$$

where $\Phi$ is defined below.

| Style | $\Phi$ | Fit Parameters |
|---|---|---|
| CPPB.0 (eV) | $\Phi = A_n$ | Ampn = $A_n$ (dimensionless), Enn = $E_{gn}$ (eV), Brn = $\Gamma_n$ (eV), mun = $\mu_n$ = −½, , 0, ½; Phasen = $\theta_n$ (dimensionless) |
| CPPB.5 (cm$^{-1}$) | | Ampn = $A_n$ (dimensionless), Enn = $E_{gn}$ (cm$^{-1}$), Brn = $\Gamma_n$ (cm$^{-1}$) mun = $\mu_n$ = −½, , 0, ½; Phasen = $\theta_n$ (dimensionless) |
| CPPB.1 (eV) | $\Phi = \dfrac{A_n}{\Gamma_n}$ | Ampn = $A_n$ (eV), Enn = $E_{gn}$ (eV), Brn = $\Gamma_n$ (eV), mun = $\mu_n$ = −½, , 0, ½; Phasen = $\theta_n$ (dimensionless) |
| CPPB.6 (cm$^{-1}$) | | Ampn = $A_n$ (cm$^{-1}$), Enn = $E_{gn}$ (cm$^{-1}$), Brn = $\Gamma_n$ (cm$^{-1}$) mun = $\mu_n$ = −½, , 0, ½; Phasen = $\theta_n$ (dimensionless) |
| CPPB.2 (eV) | $\Phi = \dfrac{A_n E_n}{\Gamma_{nn}}$ | Ampn = $A_n$ (dimensionless), Enn = $E_{gn}$ (eV), Brn = $\Gamma_n$ (eV), mun = $\mu_n$ = −½, , 0, ½; Phasen = $\theta_n$ (dimensionless) |
| CPPB.7 (cm$^{-1}$) | | Ampn = $A_n$ (dimensionless), Enn = $E_{gn}$ (cm$^{-1}$), Brn = $\Gamma_n$ (cm$^{-1}$) mun = $\mu_n$ = −½, , 0, ½; Phasen = $\theta_n$ (dimensionless) |

Tguy:

$$\varepsilon_{Tanguy\_n} = \frac{A_n \sqrt{R_n}}{(E + i\Gamma_n)^2} \{g_u(\xi(E + i\Gamma_n)) + g_u(\xi(-E - i\Gamma_n)) - 2g_u(\xi(0))\},$$

where $$g_a(\xi) = 2\ln\xi - 2\pi\cot(\pi\xi) - 2\psi(\xi) - 1/\xi$$

$$\xi(z) = \sqrt{\frac{R_a}{E_{x\_a} - z}}, \text{ and}$$

$$\psi(z) = \frac{d(\ln\Gamma(z))}{dz} \text{ (digamma function)}$$

| Style | Fit Parameters |
|---|---|
| Tguy.0 (eV) | Ampn = $A_n$ (eV$^2$), Egn = $E_{g,n}$ (eV), Bn = $\Gamma_n$ (eV), Rn = $R_n$ (eV) Ingn = |

Psemi-E0 [only PS-E0.0 (eV) Style available]:

| Fit Parameter | Description | Dimensions |
|---|---|---|
| Amp | Amplitude of $\epsilon_2$ at Egap | Amp$_n$ = Ampn (dimensionless) |
| Egap | Bandgap Energy | Egap$_n$ = Egapn (eV) |
| Br | Broadening (Gaussian type)* | Br$_n$ = Brn (eV) |
| Ewid | Width of absorption region (Egap to high energy cut-off) | Ewid$_n$ = Ewidn (eV) |
| Mpos | Connecting point of polynomials, (as a fraction of Ewid), measured from (Egap + Ewid)* | Mpos$_n$ = Mposn (dimensionless) |
| Mamp | Amplitude at connecting point of polynomials (as a fraction of Amp)* | Mamp$_n$ = Mampn (dimensionless) |
| O2nd | Second order polynomial factors* | O2nd$_n$ = O2nd (dimensionless) |

For additional insight see the J.A. Woollam Co. WVASE32 (Registered Trademark), Manual which describes the GENOSC™ Layer. Said J.A. Woollam Co. WVASE32 Manual is incorporated by reference herein. Also note that insight to the application of the Drude Model with mean scatteing time and resistivity as parameters is given in "Introduction to Solid Stae Physics", Kittel, 6th Ed, John Wiley & Sons, (1986), P. 257. More insight to the Tauc-Lorentz Model can be found in "Parameterization of the Optical Functions of Amorphous Materials in the Interband Region", Jellison & Modine, Appl. Phys. Lett. 69, 371 (1996). More insight to the Gauss-Lorentz Model can be found in an article by Kim et al., at Phys. Rev. B 45, 11749 (1992). More information about the CPPB Critical Point Parabolic Band Model can be found in "Modulation Spectroscopy/Electric Field Effects on the Dielectric Function of Semiconductors", Handbook of Physics, Vol. 2 Editor Balkanski, North Holland Pages 125-127, (1980). More Information about CPM0, CPM1, CPm2 and CPm3 Models can be found in "Other Dispersion Relations for GaP, GAAS, GaSb, InP InAs, InSb $Al_x Ga_{1-x}$, $Ga_x As_y P_{1-y}$", J. Appl. Phys. 66, 6030 (1989). More Information about the Tangay Model can be found in "Optical Dispersion of Wannier Excitons", Phys. Rev. Lett. 75, 4090 (1995) and Errata, Phys. Rev Lett. 76, 716 (1996).

Continuing, insight to Special Properties, Usefulness and what Materials some of said Oscillator Structures are applied to are:

Tauc-Lorentz

Special Properties—Absorption is force to zero (K=0) at photon energies below Bandgap Energy (eg. Capable of asymetric absorption shape around center energy).

Useful For—UV-Visible Absorptions at Energies greater than Bandgap Energy.

Materials—UV-Visible Absorption in Amorphous and Glassy Materials. Works well with materials with an Energy Gap, including Polymers and Crystalline Semiconductors.

Gaussian

Special Properties—Absorption Tail rapidly approaches Zero beyond Full-Width-Half-Maximum (FWHM) Energies. K effectively=0.0.

Useful For—IR Molecular Vibrations (amorphous materials), UV Absorptions.

Materials—Amorphous Materials and Glasses (IR Spectral Region), Polymers (IR and UV-Visible), Crystalline Materials (UV-Visible). Works well with materials with an Energy Gap, Lorentz Special Properties—Absorption Tail approaches zero slowly beyond FWHM.

Useful For—UV Absorption in Metals, IR Active Phonons (crystalline Materials).

Materials—IR-measurements of Crystalline Materials, UV, Visible and IR Interband Absorptions.

Drude

Special Properties—Lorentz Oscillator with Center Energy=0.0, (no restoring force).

Useful For—Free Carrier Absorption (conductivity).

Materials—IR behavior of Semiconductors, Metals, and Transparent Conducting Oxides (ITO).

Gauss-Lorentz

Special Properties—Convolution between Lorentz and Gaussian Absorptions. Can smoothly vary between the two shapes.

Useful For—IR Vibrational Absorptions.

Materials—Amorphous Materials and Glasses (IR spectral region).

Glad (Gauss-lorentz-half-maximum)

Special Properties—Two Gauss-Lorentz Oscillators offset from a Common Center Energy, with Different Amplitudes.

Useful For—Asymetric Absorptions (ie. Shoulders), either TR Vibrational Absorptions or Semiconductor Critical Points.

Materials—IR Measurements of Amorphous Materials, UV Absorption around Asymetric Critical Points.

Psemi (Herzinger-johs Model)

Special Properties—Triangualr Absorption Shape found near Bandgap of Direct Gap Materials Useful For—Modeling Bandgap Region of Direct Gap Materials Materials—Semiconductors Typical Oscillator Functions for Various Materials are:

SEMI CONDUCTORS

| | |
|---|---|
| UV & VISIBLE REGIONS | Tauc-Lorentz; |
| | Gaussian; |
| | GLAD, (in Gaussian Mode, for Shoulders around Critical Points); |
| | PSEMI, (for Bandgap Regions of Direct Gap Semiconductor); |
| IR REGION | Lorentz, (IR Active Phonon Modes); |
| | Drude, (Free Carrier Absorption). |

AMORPHOUS & GLASSY MATERIALS

| | |
|---|---|
| UV & VISIBLE REGIONS | Tauc-Lorentz; |
| | Gaussian or Tauc-Lorentz (for additional small "bumps" in imaginary part of Dielectric Function); |
| IR REGION | Gaussian (IR-active Vibrational Modes); |
| | GLAD (in Gaussian Mode, for Shoulders in Vibrational Absorption Regions); |
| | Drude (Free Carrier Absorption). |

POLYMERS

| | |
|---|---|
| UV & VISIBLE REGIONS | Tauc-Lorentz |
| IR REGION | Gaussian (IR-active Vibrational Modes); |
| | GLAD (in Gaussian Mode, for Shoulders in Vibrational Absorption Regions); |
| | Drude (Free Carrier Absorption - Semiconducting Polymers). |

METALS

| | |
|---|---|
| UV & VISIBLE REGIONS | Lorentz; |
| IR REGION | Drude (Free Carrier Absorption); |
| | Lorentz (IR Band Absorptions). |

ITO

| | |
|---|---|
| UV & VISIBLE REGIONS | Tauc-Lorentz; |
| IR REGION | Drude (Free Carrier Absorption). |

Continuing, it is further known that methodology of analyzing a sample system using a beam of electromagnetic radiation with wavelengths can be applied to a sample system characterized by one or more selection(s) from the group consisting of:
is isotropic and non-depolarizing, (characterized by a Jones Matrix);
is isotropic and depolarizing;
is anisotropic and non-depolarizing;
is anisotropic and depolarizing, (thereby requiring a full Mueller Matrix characterization)
is subjected to stress;
is homegenious;
is inhomegenious;

is graded parameters;
demonstrates alloy ratio;
free carriers are present;
demonstrates interface effects;

in which the beam of electromagnetic radiation provided by said source means for providing of a beam includes electromagnetic radiation containing at least one wavelength selected from the group consisting of:
RADIO;
MICRO;
FIR;
IR;
NIR-VIS-NUV;
UV;
DUV;
VUV;
EUV;
XRAY;

characterized by a selection from the group consisting of:
it comprises a single wavelength;
it comprises multiple wavelengths;
it comprises a plurality of wavelengths which are simultaneously, or sequentially scanned individually;

and in which the beam of electromagnetic radiation is, just prior to said sample system characterized by a selection from the group consisting of:
unpolarized;
partially polarized;
randomly: polarized;
linearly polarized;
with respect to said sample system linearly "p" polarized;
with respect to said sample system linearly "s" polarized;
circularly polarized;
elliptically polarized;
polarization state is modulated;

and is caused to interact with a sample system via a selection from the group consisting of:
by reflection;
by transmission;
by both reflection and transmission;

at one or more angles of incidence, (AOI's), with respect to a surface thereof selected from the group consisting of:
normal;
oblique;

while said data detector means is utilized to detect resulting:
reflected;
transmitted;
scattered electromagnetic radiation.

The beam of electromagnetic radiation which is applied to a sample system can further be characterized by being, before and monitored after said sample system, respectively:
non-polarized incident, with measurement of intensity out;
non-polarized incident, with measurement of polarized out;
polarized incident, with measurement of intensity out;
polarized incident, with measurement of polarized out;

where "polarized" includes "partially polarized".

Further, said method of analyzing a sample system using a beam of electromagnetic radiation can have modulation applied thereto during data accumulation, said modulation being of at least one selection from the group consisting of:
Electromagnetic Beam Magnetic "B" Field;
Electromagnetic Beam Electric "E" Field;
Electromagnetic Beam Flux "$E^2$";
Ambient Environment Composition, (eg. liquid, gas);
Sample System Temperature, (which can be above or below room temperature);
Sample System Strain;
Pressure applied to Sample System.

Further, methodology of analyzing a sample system using a beam of electromagnetic radiation can involve providing polarizer means and accumulating ellipsometric PSI data while ellipsometric DELTA is placed within a range near 90 degrees via adjustment of the angle-of-incidence of the beam of electromagnetic radiation with respect to the surface of said sample system.

Detector systems applied to detect electromagnetic radiation after its interaction with a sample system can be selected from the group consisting of:
photo-diode;
photo-diode array;
semiconductor detector;
charge-coupled-device;
photo-multiplier tubes;
photo-resistive elements;
photo-conductive elements;
thermo-piles;
bolemeters.; and
having detector system distinguishing aperturing present.

It is also noted that anything having an effect on the optical response of a sample system should be modeled in a mathematical model thereof. Optical constant determining properties of a sample system which might require mathematical modeling are chemical bonds and phonon effects, the presence of a bandgap, the effect of energy band bending near a junction (eg. PN, Schottky barrier, P+P, N+N both at a surface and buried), free carrier profiles, ion implanted dopant profiles, electro-optic and/or magneto-optic effects, Kerr rotation, and etc. It is noted that various properties of a sample system are better investigated in one wavelength range. For instance, it might be best to evaluate a thin film layer thickness in the VIS wavelength range, then set said thickness value during investigations using IR wavelengths. This is an example of "coupling" parameters in different wavelength ranges can enable such as determining uncorrelated depolarization effects in the IR wavelength range, which otherwise might be attributed to a different thickness and evaluated as such in a regression procedure.

It is also noted that sample system surface roughness can be detected on many scales. Short wavelengths can detect small scale deviations from smoothness, whereas longer wavelengths detect such deviations on a larger scale.

The above discloses that it is known to investigate thin surface layers on objects with spectroscopic electromagnetic radiation, and that typically a mathematical model of the system is proposed for the entire system, and is data obtained corresponding to change in polarization state in a beam of electromagnetic radiation caused to interact with the system. A regression procedure is then performed to modify the values of parameters in the mathematical model to bring calculated results into agreement with measured data. It is also disclosed that In some cases, however, the state of a sample system as obtained, or entered into analysis, is initially unknown and proposing mathematical model therefore is not possible. For instance, it comprises a substrate which was subjected to previous processing, the specific nature of which is unknown. This can be the case, for instance, where articles are manufactured via deposition or removal of material, to or from, a process substrate.

In that light it is further disclosed that the present Invention enables application of ellipsometry to investigation of sample systems which are not easily subject to mathematical modeling by allowing definition of a Standard Result which is expected, when electromagnetic radiation is caused to interact with a sample system. This has application in manuacturing settings wherein expected ellipsometric data is known, (having been previously developed), and wherein newly manufacured sample systems are ellipsometrically investigated and data obtained compared thereto.

The present invention provides for obtaining ellipsometric data from a sample system and therefrom defining "Standard" ellipsometic data for data obtained from such sample systems. Data obtained from future sample systems of the same kind is then compared to said Standard data.

It is noted that the J.A. Woollam Co. WVASE Program has had the capability to determine Pseudo-Refractive Index and Pseudo-Extinction Coefficients for years. What that means is that for a sample system comprising many layers, each of which has determinable Refractive Index and Extinction Coefficients, it is possible to determine a "Global" representation which does not require determining specific Refractive Index and Extinction Coefficients for each layer. The sample system is in effect considered to be uniform with overall Refractive Index and Extinction Coefficients, which are therefore termed "Pseudo". Said Psuedo Parameters are suitable for application in the present invention methodology. This takes the from of Psuedo Parameters for a Sample being obtained and defined as Standard Data for a Standard Sample. Ellipsometric Data are then obtained from Samples which are meant to be identical to the Standard Sample, and the Psuedo Parameters compared thereto. If the comparison is favorable then it is acepted that the Samples are indeed sbstantially identical.

As a specific example, in the IR range of wavelengths it can happan that sequentially obtained data sets of say Intensity vs. Wavelength, from the same sample system show generally similar patterns. Specific magnitudes at-specific wavelengths might differ. A present invention approach is to provide a "Composit" by perhaps finding an average Intensity at each Wavelength for some number of sequentially obtained data sets which are similarly obtained. The Composit data is then used as a reference to which data obtained from other similar sample systems is compared. If comparison shows substantially similar characteristics then the similar sample system can be acceptance. If, however, the Data shows the presence of non-correspondence, the sample systems can be determined to be non-similar. The point to be taken is that no mathematical model evaluation of specific layer thickneses and optical constants and/or surface rougness and/or concentration grading etc. is required. A method of applying ellipsometry to determine similarity between a standard sample system and test sample systems can then comprise the steps of:

a) providing a standard sample system, obtaining ellipsometric data and therefrom defining standard sample system data;

b) providing a second sample system, obtaining ellipsometric data therefrom and comparing it to the standard sample system data;

c) based upon the comparison determining similarity or difference between the standard and second sample systems.

The standard data comprises determined pseudo-refractive index and psuedo extinction coefficient; and statistical methods can be used to determine similarity or difference between the standard and second sample systems.

Background Prior Art References in Spectroscopic Ellipsometry.

"Proceedings of the 1st international conference on spectroscopic ellipsometry", Paris, France January 1993, Spectroscopic Ellipsometry, published by Elsevier, Sequoia, Amsterdam, The Netherlands. Also, published in Thin Solid Films, volumes 233 and 234, 1993. Editors are A. C. Boccara, C. Pickering, and J. Rivory. The papers are published in groups by the following sub-topics:

Reflectance anisotropy: 6 papers
Roughness and electroschemistry: 13 papers
Semiconductors and microelectronics: 31 papers
In situ characterization and nucleation and growth: 14 papers
Infrared ellipsometry: 13 papers
Novel techniques and analysis: 10 papers
Modeling of data: 12 papersSE on liquids: 5 papers
optical properties of materials and anisotropy effects: 19 papers.

"May 1997 2nd international conference on Spectroscopic Ellipsometry", held in Clarleston, South Carolina has several hundred papers on SE. The papers are published as a book, Spectroscopic Ellipsometry, and as a special edition of Thin Solid Films journal, volumes 313 and 314, 1998 by Elsevier Science S.A. Lausanne Switzerland. Editors are R. W. Collins, D. E. Aspnes, and E. A. Irene. The paper topics are:

Plenary reviews of SE history and piezo-optical effects: 2 papers
Ellipsometric instrumentation; Error and data analysis: 24 papers
Optical properties of solids and thin films from SE: 15 papers
Material and structural analysis by SE: 16 papers
Anisotropic and inhomogeneous solids and thin films: 13 papers
Ellipsometry for in situ and real-time measurements, monitoring, and control of materials preparation and processing: 23 papers
Optics of semiconductors: surfaces, interfaces, and quantum structures: 20 papers
Infrared and Ultraviolet SE: 24 papersSE in chemistry, biochemistry and electrochemistry: 14 papers.

"3rd international conference on spectroscopic ellipsometry", held in Vienna, Austria July 2003. The papers were published as a book titled "Spectroscopic Ellipsometry", and as a special issue of the Thin Solid Film Journal by Elsevier, Editors Fried et al., Vols. 455 and 456, (May 2004).

Sub-topics are:
Reviews: 3 papers
Infrared and ultraviolet SE: 18 papers
Industrial applications: 22 papers
Advanced instrumentation, including polarimetry and scatterometry: 27 papers
Biological and medical applications: 8 papers
Anisotropic and thin films: 28 papersIn situ and real-time: 19 papers
Reflection anisotropy: 10 papers
Semiconductors: 17 papers
Surfaces, interfaces and thin films: 44 papers
Polymers: 78 papers Need remains for a methodology of characterizing sample systems utilizing wavelengths over a large wavelength range.

DISCLOSURE OF THE INVENTION

The disclosed invention comprises a method of simultaneously evaluating a plurality of parameters in a mathematical model of a sample system which describes the effect said sample system will have on electromagnetic radiation which is caused to interact therewith. Said method involves regression of the mathematical model onto data obtained by application of electromagnetic radiation to the sample system, at least one of said parameters in said mathematical model being subject to accurate evaluation using data obtained by applying one range of wavelengths selected from the group consisting of:
  RADIO;
  MICRO;
  FIR;
  IR;
  NIR-VIS-NUV;
  UV;
  DUV;
  VUV;
  EUV;
  XRAY;
to said sample system, but not by using data obtained by applying another range of wavelengths in said group to said sample system.

Said method comprises the steps of:
  a) providing a sample system and a mathematical model thereof which characterizes the effect said sample system will exert on electromagnetic radiation caused to be incident thereupon;
  b) providing at least one source of electromagnetic radiation, said at least one source of electromagnetic radiation having the capability of providing electromagnetic radiation in at least two ranges selected from the group consisting of:
    RADIO;
    MICRO;
    FIR;
    IR;
    NIR-VIS-NUV;
    UV;
    DUV;
    VUV;
    EUV;
    XRAY;
  c) simultaneously or sequentially applying incident electromagnetic radiation from said at least two selected ranges of electromagnetic radiation to said sample system such that after interaction with said sample system via reflection and/or transmission, electromagnetic radiation from each of said at least two selected ranges of electromagnetic radiation is caused to enter at least one detector sensitive thereto, which at least one detector provides as output data which characterizes the influence exerted by the sample system on the incident electromagnetic radiation;
  d) simultaneously regressing the mathematical model onto the data provided by said at least one detector to the end that the parameters in the mathematical model are evaluated, including said at least one parameter which is subject to accurate evaluation using data in one range of wavelengths selected from the group consisting of:
    RADIO;
    MICRO;
    FIR;
    IR;
    NIR-VIS-NUV;
    UV;
    DUV;
    VUV;
    EUV;
    XRAY;
but not by using data in another range of wavelengths in said group.

The step of providing said at least one source of electromagnetic radiation can involve providing a source of FIR or IR, and a source of other than FIR or IR wavelength radiation, at least one of said sources being a part of an ellipsometer system which provides electromagnetic radiation of a known polarization state to said sample system.

The step of providing said at least one source of electromagnetic radiation, can involve providing a source of NIR-VIS-NUV, and a source of other than NIR-VIS-NUV wavelength radiation, at least one of said at least one source being a part of an ellipsometer system which provides electromagnetic radiation of a known polarization state to said sample system.

The step of providing said at least one source of electromagnetic radiation can involve providing a source of UV, and a source of other than UV wavelength radiation, at least one of said at least one source being a part of an ellipsometer system which provides electromagnetic radiation of a known polarization state to said sample system.

The step of providing said at least one source of electromagnetic radiation can involve providing a source of DUV, and a source of other than DUV wavelength radiation, at least one of said at least one source being a part of an ellipsometer system which provides electromagnetic radiation of a known polarization state to said sample system.

The step of providing said at least one source of electromagnetic radiation can involve providing all wavelengths, RADIO; MICRO; FIR, IR, NIR, VIS, NUV, UV, DUV, EUV and XRAY.

The step of providing said at least one source of electromagnetic radiation can involve providing wavelengths in the FIR, IR, UV, DUV, EUV and XRAY.

The step of providing said at least one source of electromagnetic radiation can involve providing wavelengths from any combination of sources of electromagnetic radiation.

The step of simultaneously or sequentially applying incident electromagnetic radiation from said at least two selected ranges of electromagnetic radiation can involve obtaining reflection data and/or transmission data.

The step of simultaneously regressing the mathematical model onto the data provided by said at least one detector can involve a selection from the group consiting of:
  a) point by point evaluation where the parameters in the mathematical model are evaluated at each wavelength;
  b) application of parameterization and evaluation of the parameters in the mathematical model wherein the parameters are evaluated simultaneously at a plurality of wavelengths;
  c) use of both the point by point and parameterization evaluation approaches in a and b.

Another recital of a disclosed method involves providing a continuous plot of at least one optical constant of a sample system system, which at least one optical constant does not demonstrate discontinuities over a range of wavelengths from the FIR through the NIR-VIS-NUV, UV and into the DUV. The method involves regression of a mathematical model containing said optical constant as a parameter onto data obtained by application of electromagnetic radiation to said sample system either simultaneously or sequentially in the ranges of wavelengths from the IR through the NIR-VIS-NUV, UV, DUV, EUV into the XRAY, and comprises the steps of:

a) providing a sample system and a mathematical model thereof which includes said at least one optical constant, which mathematical model characterizes the effect said sample system will exert on electromagnetic radiation caused to be incident thereupon;

b) providing at least one source of electromagnetic radiation, said at least one source of electromagnetic radiation having the capability of providing electromagnetic radiation in the range of FIR through NIR-VIS-NUV, UV, DUV, EUV and into the XRAY;

c) simultaneously or sequentially applying incident electromagnetic radiation from said at least one source such that after interaction with said sample system via reflection and/or transmission, electromagnetic radiation from each of said ranges of electromagnetic radiation is caused to enter at least one detector sensitive thereto, which at least one detector provides as output data which characterizes the influence exerted by the sample system on the incident electromagnetic radiation;

d) simultaneously regressing the mathematical model onto the data provided by said at least one detector to the end that the optical constants of the sample system system are evaluated over a plurality of ranges of IR through NIR-VIS-NUV, UV, DUV, EUV and into the XRAY.

Another aspect of the disclosed invention is a method of determining the optical constants of a sample system comprising a substrate with at least one thin film on a surface thereof, utilizing a spectroscopic beam of electromagnetic radiation including wavelengths from at least two selections from the group consisting of:
RADIO;
MICRO;
FIR;
IR;
NIR-VIS-NUV;
UV;
DUV;
VUV;
EUV;
XRAY;

said method comprising the steps of:
a) obtaining ellipsometric data over a spectroscopic range and displaying said data as an ellipsometric parameter vs. a parameter which varies with wavelength, said plot being characterized by a range corresponding to longer wavelengths in which at least one thin film is substantially transparent and a range corresponding to shorter wavelengths in which said plot demonstrates absorption effects and typically interference resulting from reflections from the surface and at least one thin layer interface therebelow;

b) proposing a mathematical model of said sample system, said mathematical model comprising parameters which enable evaluating a selection from the group consisting of:
refractive index and-extinction coefficient, and
real and imaginary parts of the dielectric function;

and generating data corresponding to the data in step a from said mathematical model and effectively displaying said generated data with said obtained ellipsometric data over the spectroscopic range;

c) selecting a range in said plots in which substantial absorption effects, and interference effects are not present and simultaneously performing regression over said range to set parameter values in said mathematical model to values such that the plots of the obtained and generated data are substantially the same;

d) fixing the value of at least one parameter obtained in step c, and setting the range of wavelengths or energy or wave number to a selection from the group consisting of:
the entire obtained spectroscopic range; and
a portion-of the spectroscopic range including the range in which absorption effects are dominant and a portion of the spectroscopic range in which absorption
effects are not dominant;

and setting parameters which allow determining values for a selection from the group consisting of:
refractive index and extinction coefficient, and
real and imaginary parts of the dielectric function;

then performing a point by point fit begining in the range wherein absorption effects are not dominant, such that a refractive index and extinction coefficient is determined over said spectroscopic range.

The parameter which varies with wavelength is typically plotted as a selection from the group consisting of:
wavelength;
energy; and
wave number.

Another recitation of a disclosed invention method of determining the optical constants of a sample system comprising a substrate with at least one thin film on a surface thereof, utilizing a spectroscopic beam of electromagnetic radiation, comprising the steps of:
a) obtaining ellipsometric data over a range of spectroscopic wavelengths and displaying said data as an ellipsometric parameter vs. a selection from the group consisting of:
wavelength;
energy;
wave number;

said plot being characterized by a range corresponding to longer wavelengths in which said at least one thin film is substantially transparent and a range corresponding to shorter wavelengths in which the plot demonstrates absorption, and the results of interference resulting from reflections from the surface and at least one thin layer interface therebelow;

b) proposing a mathematical model of said sample system, said mathematical model comprising, and parameters which allow evaluating a selection from the group consisting of:
refractive index and extinction coefficient;
real and imaginary parts of the dielectric function;

as fit parameters, and generating data corresponding to the data in step a, from said mathematical model and displaying said generated data with said obtained ellipsometric data over the spectroscopic range;

c) selecting a range of wavelengths or energy or wave number in which substantial absorption and minimal interference effects are not present and simultaneously performing regression over said range of wavelengths or energy or wave number to set parameter values in said mathematical model to values such that the plots of the obtained and generated data are substantially the same;

d) fixing at least one parameter value obtained in step c, and setting the range of wavelengths or energy or wave number to include at least some the obtained data range in which absorption, and minimal interference effects are present in the obtained data, and setting parameters selected from the group consisting of:
refractive index and extinction coefficient; and
real and imaginary parts of the dielectric function;

as fit parameters,.then performing a point by point fit begining at long wavelength, (ie. low energy or wave number), such that a refractive index and extinction coefficient is determined at each wavelengths or energy or wave number over the range of the obtained data wherein absorption effects are not dominating and at minimal interference effects are present.

Step d can be performed at least one additional time with the range of wavelengths or energy or wave number set to include more of the obtained data range in which minimal interference effects are present in the obtained data, or the entire obtained data range in which interference effects are both present and not present in the obtained data. The determination as to when use the whole range of obtained data is determined based on results determined by trying it. If the point by point fit does not provide good results when the whole range of data is selected, then smaller steps into the range of data wherein absorption effects are not dominating and interference efects are present must be used.

The mathematical model can often be beneficially set to comprise a Cauchy or Sellemier function to represent the thin film in the transparent region of wavelengths.

It can also be beneficial to provide ellipsometric data obtained at at least two angles of incidence.

The method can further comprises saving the optical constants determined over the entire range of wavelengths or energy or wave number etc., and replacing the mathematical model of the thin layer with a mathematical model which allows fitting the refractive index or the imaginary part of the dielectric function with Mathematical Dispersion Models such as Kramers-Kronig consistent oscillators, plotting said refractive index or imaginary part of the dielectric function and fitting said refractive index or imaginary part of the dielectric function with at least one Mathematical Dispersion Model and performing a regression to evaluate parameters in said mathematical model.

The method can also further comprise saving determined optical constants over the entire range of wavelengths or energy or wave number, and replacing the mathematical model of the thin layer with a mathematical model which allows fitting the refractive index and extinction coefficient or the real and imaginary parts of the dielectric function with Mathematical Dispersion Models such as Kramers-Kronig consistent oscillators, plotting said refractive index or imaginary part of the dielectric function and fitting said refractive index or imaginary part of the dielectric function with at least one oscillator, and performing a regression to simultaneously evaluate refractive index and extinction coefficient or real and. imaginary parts of the dielectric function parameters in said mathematical model.

Another method of determining the optical constants of a sample system comprising a substrate with a thin film on a surface thereof, utilizing a spectroscopic beam of electromagnetic radiation, comprises the steps of:

a) obtaining spectroscopic ellipsometric data for said sample system at at least one angle of incidence by causing a spectroscopic beam of electromagnetic radiation including wavelengths from at least two ranges selected from: RADIO; MICRO FIR; IR; NIR-VIS-NUV; UV; DUV; VUV; EUV; and XRAY; to interact with said sample system and enter a detector;

b) determining a range of wavelengths over which said thin film is sunstantially transparent and determining the thickness of said thin film utilizing ellipsometric data obtained in said region by applying a Cauchy or Sellmeier optical model and a square error minimizing regression to evaluate parameters therein;

c) fixing the thickness determined in step b, and obtaining a preliminary set of optical constants comprising:
$(e1(\lambda)+ie2(\lambda))$ by point by point fitting to data across the entire measured spectral range, and saving the resulting data;

d) while maintaining thickness fixed, applying at least one mathematical dispersion model to said saved results and evaluating parameters therein via regression onto the $e2(\lambda)$ data only, e) while maintaining thickness fixed and using the results obtained in step d as initial conditions, performing a regression onto $(e1(\lambda)+ie2(\lambda))$ data;

f) applying a global regression onto at least $e2(\lambda)$ data to fit all parameters, including thickness, over the entire spectral range;

g) modifying the mathematical model and repeating steps a-f at least once.

Parametric Dispersion models can be selected from the non-limiting group consisting of: Cauchy; Cauchy+Urbach absorption; Sellmeier Oscillator, (zero broadened); Lorentz Oscillator; Gaussian Oscillator; Harmonic Oscillator; Drude Oscillator; Tauc-Lorentz Oscillator; Cody-Lorentz Oscillator; Tanguay; Ionic Oscillator; TOLO; Gauss-Lorentz Oscillator; Gauss-Lorentz Oscillator Asymetric Doublet (Glad) Oscillator; Herzinger-Johs Parametric Semiconductor Oscillator Model; Psemi-Eo oscillator; Critical Point Parabolic band (CPPB); Adachi Oscillator Model; Pole;

where the Oscillators are preferably Kramer-Kronig consistent.

(Note, said Oscillator Structures are described in the J.A. Woollam Co. WVASE Manual, which is incorporated by reference herein. (WVASE is a Registered Tradeamrk of the J.A. Woollam Co. Inc.).

The method can further comprise including parameters in said mathematical model which characterize at least one selection from the group consisting of:
surface roughness;
optical constant grading;
anisotropy;
at least one interface layer;
thin film composition, (EMA);

said thin film composition being characterized by at least one selection selected from the group consisting of;
thin film porosity;

alloy ratio;
thin film crystalinity;
depolarization factor.

The method can further comprise including parameters in said mathematical model which characterize thin film composition, and said Effective Media Mathematical-Model can be selected from the group consisting of:
Lorentz-Lorenz;.
Maxwell-Garnett;
Bruggeman;
Linear.

The method can further comprise including parameters in said mathematical model which characterize sample system anisotropy and/or optical constant grading.

The method can further comprise including parameters in said mathematical model which characterize at least one selection from the group consisting of:
thin film non-uniformity;
electromagnetic beam wavelength bandwidth spread;
spread in electromagnetic beam angle of incidence.

The method can further comprise including parameters in said mathematical model which characterize sample system caused incoherent effects, including reflections from that back of transparent sample systems.

The method can further comprise including parameters in said mathematical model which characterize sample system composition effects (eg. alloy ratios).

The method can further comprise including parameters in said mathematical model which characterize sample system caused incoherent effects based upon patterns being present thereupon and reflections from interfaces and back surfaces-of transparent sample systems.

The method can further comprise including parameters in said mathematical model which characterize sample system caused rotary effects.

The method can further comprise including parameters in said mathematical model which characterize magneto-optic or electro-optic effects on a sample system.

The method can further comprise including parameters in said mathematical model which characterize sample system temperature effects.

The method can further comprise selecting staring numbers for parameters in the mathematical model which are input to the regression procedure by a method that tests mean square error after a small number of itterations for a segence of starting values.

Data utilized by the disclosed invention to determine sample system PSI or DELTA can be characterized by being:
obtained from multiple sample systems;
obtained at multiple angles-of-incidence (AOI's);
obtained at multiple sample system orientations;
obtained using focused or unfocused beam;
obtained in-situ or ex-situ;
obtained as a function of temperature;
obtained as a function of magnetic or electric field.

The foregoing assumes that a mathematical model of a sample system, which contains parameters to be evaluated, can be postulated prior to performing a regression procedure onto acquired data. While inclusive of the foregoing teachings, the disclosed invention is not limited to application in said case, and further includes a method of ellipsometrically characterizing surface material present on an article manufactured by the deposition or removal of material, to or from, a process substrate, said method requiring no explicit knowledge of prior process substrate composition. That is, the step of providing a mathematical model can be replaced by the step or steps of obtaining data at at least two times' during sample system processing and using said data to predict results at another time, and then proceeding vith application of a regression procedure to bring the predicted result into agreement with data. The outer surface material is modeled mathematically by analytic model Fresnel equations. Said method can be generally understood as comprising the steps of;

a) providing a material deposition and/or removal chamber, and an ellipsometer system configured with respect thereto so as to, in use, cause a beam of electromagnetic radiation to impinge upon an article therewithin during a procedure in which material deposition to, or removal from, a process substrate is caused to occur over a period of time:

a') at at least two times causing said ellipsometer system to cause a beam of electromagnetic radiation to impinge upon the article such that sufficient ellipsometric data to evaluate variable parameters which characterize the optical response of the article is acquired, said data being characterized by:
it is acquired at at least two wavelengths, each selected from a different range in the group consisting of:
RADIO;
MICRO;
FIR;
IR;
NIR-VIS-NUV;
UV;
DUV;
VUV;
EUV;
XRAY;

a") in conjunction with the foregoing steps, providing a system of variable parameter containing analytic equations which describe interaction of electromagnetic radiation with a layered material system;

b) utilizing said sufficient ellipsometric data obtained in step a' and said system of variable parameter containing analytic equations provided in a", to predict ellipsometric characterization of said article at a prediction time which is different from either of said at least two times of step a;

c) during material deposition or removal, to or from, a process substrate, obtaining ellipsometric data at a time corresponding to the prediction time of step b; and d) utilizing said ellipsometric data obtained in step c in a minimization algorithm to provide values for the variable parameters in at least one selection from the group consisting of:
said variable parameters in said variable parameter containing analytic equations which describe interaction of electromagnetic radiation with a layered material system provided in step a"; and
said variable parameters identified in step a' which characterized the optical response of the article;

at said prediction time in step b;

and interpreting the resulting values for said variable parameters to characterize surface material of said article at the time data was obtained in step c.

A more specific recital of the disclosed invention method of characterizing the outermost material of an article manufactured by the deposition or removal of material, to or from, a process substrate, without explicit knowledge of any previously deposited underlying layers, comprises the steps of:

a) providing a material deposition or removal chamber and an ellipsometer system configured with respect thereto so as to, in use, cause a beam of polarized electromagnetic radiation to impinge upon a process substrate therewithin during a procedure in which material deposition or removal upon said process substrate is caused to occur over a period of time;

a') obtaining ellipsometric data during material deposition or removal upon said process substrate at three distinct times (t1), (t2), and (t3);

b) using a system of analytic equations which are derived from the exact Fresnel equations that describe the interaction of electromagnetic radiation with a layered material system, such analytic equations not requiring any knowledge of the underlying layer structure previously deposited on the sample system, calculating ellipsometric data at time (t3), using the ellipsometric data acquired at times (t1) and (t2), and a parameterized optical model for the outermost material deposition or removal that occurs between (t1) and (t3), and (t2) and (t3);

c) determining the optical model parameters which characterize the outermost layer(s) by minimizing the difference between the ellipsometric data calculated at time (t3) by the analytical equations in b) and the ellipsometric data measured at time (t3), using a minimization algorithm.

Note that the foregoing method specifically requires that data be obtained at Three (3) different times. The following recites disclosed invention methodology for the case in which data is obtained at Four (4) different times.

A method of characterizing the outermost material of an article manufactured by the deposition or removal of material, to or from, a process substrate, without explicit knowledge of any previously deposited underlying layers, comprising the steps of:

a) providing a material deposition or removal chamber and an ellipsometer system configured with respect thereto so as to, in use, cause a beam of polarized electromagnetic radiation to impinge upon a process substrate therewithin during a procedure in which material deposition or removal upon said process substrate is caused to occur over a period of time;

a') obtaining ellipsometric data during material deposition or removal upon said process substrate at four distinct times (t1), (t2), (t3), and (t4);

b) using a system of analytic equations which are derived from the exact Fresnel equations that describe the interaction of electromagnetic radiation with a layered material system, such analytic equations not requiring any knowledge of the underlying layer structure previously deposited on the sample system, calculating ellipsometric data:

at time (t1), using the ellipsometric data acquired at times (t2) and (t4), and a parameterized optical model for the outermost material deposition or removal that occurs between (t1) and (t2), and (t1) and (t4);

at time (t2), using the ellipsometric data acquired at times (t1) and (t3), and a parameterized optical model for the outermost material deposition or removal that occurs between (t2) and (t1), and (t2) and (t3);

at time (t3), using the ellipsometric data acquired at times. (t2) and (t4), and a parameterized optical model for the outermost material deposition or removal that occurs between (t3) and (t2), and (t3) .and (t4);

at time (t4), using the ellipsometric data acquired at times (t1) and (t3), and a parameterized optical model for the outermost material deposition or removal that occurs between (t4) and (t1), and (t4) and (t3);

c) determining the optical model parameters which characterize the outermost layer(s) by minimizing the differences between the ellipsometric data calculated at times (t1), (t2), (t3), and (t4) by the analytical equations in b) and the ellipsometric data measured at times (t1), (t2), (t3), and (t4) using a minimization algorithm.

The following recites the disclosed invention methodology for the case in which data is obtained at more than three different times.

A method of characterizing the outermost material of an article manufactured by the deposition or removal of material, to or from, a process substrate, without explicit knowledge of any previously deposited underlying layers, comprising the steps of:

a) providing a material deposition or removal chamber and an ellipsometer system configured with respect thereto so as to, in use, cause a beam of polarized electromagnetic radiation to impinge upon a process substrate therewithin during a procedure in which material deposition or removal upon said process substrate is caused to occur over a period of time;

a') obtaining ellipsometric data during material deposition or removal upon said process substrate at at least three distinct times {t1, t2, t3 . . . tn};

b) using a system of analytic equations which are derived from the exact Fresnel equations that describe the interaction of electromagnetic radiation with a layered material system, such analytic equations not requiring any knowledge of the underlying layer structure previously deposited on the sample system, calculating ellipsometric data:

at one time selected from the set of ellipsometric data points chosen in a'), using the ellipsometric data acquired at two other times from the set of ellipsometric data points chosen in a'), and a parameterized optical model for the outermost material deposition or removal that occurs between the selected times;

optionally at additional times selected from the set of ellipsometric data points chosen in a'), using the ellipsometric data acquired at two other times from the set of ellipsometric data points chosen in a'), and a parameterized optical model for the outermost material deposition or removal that occurs between the selected times;

c) determining the optical model parameters which characterize the outermost layer(s) by minimizing the differences between the ellipsometric data calculated at the selected times by the analytical equations in b) and the ellipsometric data measured at the selected times using a minimization algorithm.

The minimization algorithm can be implemented by non-linear regression, and preferably the minimization algorithm is the Levenberg-Marquardt method.

The optical model for the outermost material deposition or removal can be parameterized by at least one of the parameters from the selected list:

the material deposition rate,
the material removal rate,
the optical constants of the outermost material, the surface roughness of the outermost material.

The process substrate can be of a shape selected from the group consisting of:
   comprising a planar surface;
   of an arbitrary shape.

It is also within the scope of the disclosed invention to provide a wittness sample system onto which material is deposited, said wittness sample system having a relatively thick transparent material thereupon onto which said material is deposited. Th reason for this is that ellipsometry is far more sensitive to ultrathin deposited layers when they are deposited onto such a wittness sample system.

Finally is is to be understood that the method step of obtaining ellipsometric data can be characterized by at least one selection from the group consisting of:
   it is acquired at a single wavelength;
   it is acquired at a more than one wavelength;
   it is acquired at a a single angle of incidence;
   it is acquired at at least two angles of incidence of the ellipsometric electromagnetic beam to the surface of the process substrate.

For the purpose of the presently disclosed invention, however, wavelenghts from at least two ranges selections from the group consisting of:
   RADIO;
   MICRO;
   FIR;
   IR;
   NIR-VIS-NUV;
   UV;
   DUV;
   VUV;
   EUV;
   XRAY;
are utilized.

It is also disclosed that where investigated films are very thin, (eg. less than 100 Angstroms), it becomes difficult to identify content in spectroscopic data which is definitely correlated to thin film characterizing parameters, such as dielectric constant and/or thickness. The disclosed invention comprises a method of investigating a sample'system comprised of at least one thin layer of material on a substrate, which thin layer has a thicknesses on the order of less than about 100 Angstroms. One embodiment of said method comprises the steps of:
   a) providing two sample systems, at least one of which comprises at least one thin layer of material thereon;
   b) obtaining ellipsometric data for.each of the sample systems;
   c) subtracting the obtained spectra from one another;
   d) analyzing the difference spectra obtained in step c to identify thin film characterizing aspects which are not easily identifiable in the step b spectra.

An application of the disclosed invention is in real time fabrication of sample systems comprising a sequence of high and low "K" dielectric constant layers of materials which have thicknesses on the order of 100 Angstroms, said method comprising the steps of:
   a) fabricating a reference sample system which comprises a sequence of high and low "K" dielectric constant layers;
   b) obtaining spectroscopic data therefrom as said reference sample is fabricated;
   c) fabricating a second sample system which is meant to be the same as the reference sample;
   d) obtaining spectroscopic data from said second sample system as it is fabricated and in real time detecting differencs in said spectra as compared to the corresponding reference sample system spectroscopic data; and
   e) modifying fabrication parameters to minimize said differences.

Said method is preferably, though not limited to, utilizing spectroscopic data which corresponds to, or is derived from Ellipsometric PSI ($\Psi$) and/or DELTA ($\Delta$) vs. Wavelength. As discussed in more detail in the Detailed Description Section of this Specification, N, C and S parameters, which are derived from PSI ($\Psi$) and DELTA ($\Delta$) are often easier to utilize, said N, C and S being:

$N=\text{Cos}(2\Psi)$;

$C=\text{Sin}(2\Psi)\text{Cos}(\Delta)$;

$S=\text{Sin}(2\Psi)\text{Sin}(\Delta)$.

It is also noted that typical, though non-limiting, thin layers on a sample system which has a sequence of high and low "K" dielectric constant layers present thereupon, can comprise at least one selection from the group consisting of:
   $SiO_2$;
   SiON;
   HfO;
   $HfO\text{-}SiO_2$.

Another example of the disclosed invention method provides that where a thin film being formed on a sample system substrate is to be monitored during its formation, a witness sample system is also provided onto which the same thin film is formed. The witness sample system is monitored and results obtained therform are used to characterize the thin film on the sample system substrate. Importantly, the witness sample system need not be of the same composition as is the sample system substrate. In fact, it has been found very beneficial to intentionally provide a witness sample system which comprises a thick dielectric, (eg. greater than about 250 Angstroms and preferably greater than 1000 Angstronms), onto which the thin film is deposited. It is found that a very benefical method for evaluating thickness of an ultrathin film then comprising the steps of:
   a) providing a system comprising an optically absorbing substrate with a layer of optically transparent material on a surface thereof which is greater than about 250 Angstroms deep;
   b) causing a beam of spectroscopic electromagnetic radiation to impinge on said surface of said optically transparent material at an oblique angle, interact with said system and via a detector determining spectroscopic ellipsometic PSI ($\Psi$) and DELTA ($\Delta$), and therefrom calculating at least one selection from the group consisting of:

$N_O=\text{Cos}(2\Psi)$;

$C_O=\text{Sin}(2\Psi)\text{cos}(\Delta)$;

$S_O=\text{Sin}(2\Psi)\text{Sin}(\Delta)$;

c) depositing an ultrathin film of absorbing material on a surface of said layer of optically transparent material and again causing a beam of spectroscopic electromagnetic radiation to impinge on said surface of said optically transparent material at an oblique angle, interact with said system and via a detector obtaining spectroscopic ellipsometic PSI (Ψ) and DELTA (Δ), and therefrom calculating at least one selection from the group consisting of:

$N_f = \cos(2\Psi)$;

$C_f = \sin(2\Psi)\cos(\Delta)$;

$S_f \sin(2\Psi)\sin(\Delta)$;

d) over a spectroscopic range of wavelengths determining a parameter vs. wavelength which depends on at least one difference selected from the group consisting of:

$(N_f - N_O)$ $(C_f - C_O)$; and $(S_f - S_O)$;

e) using peaks in the parameter determined in step d to evaluate thickness of the ultrathin film.

The parameter determined in step d can be an RMS value calculated from:

$$\sqrt{\frac{(N_f - N_o)^2 + (C_f - C_o)^2 + (S_f - S_o)^2}{3}};$$

Note that the just recited example can be benefically applied to the case where a MOSFET Gate metalization is being deposited to a substrate on which is present less than 100 Angstroms of Gate Oxide or other Gate insulator material. The Witness Sample, having a much thicker layer of Oxide or other Insulator, enables acquisition of a spectra which makes the detection of the thickness of the deposited metal much more pronounced. The effect is demonstrated graphically in the Detailed Description Section of this Specification, using Amorphous Silicon and Amorphous Carbon thin films on thick transparent dielectric.

The disclosed invention will be better understood by reference to the Specification in conjunction with the Drawings, and the Claims.

DETAILED DESCRIPTION

Figure 1:
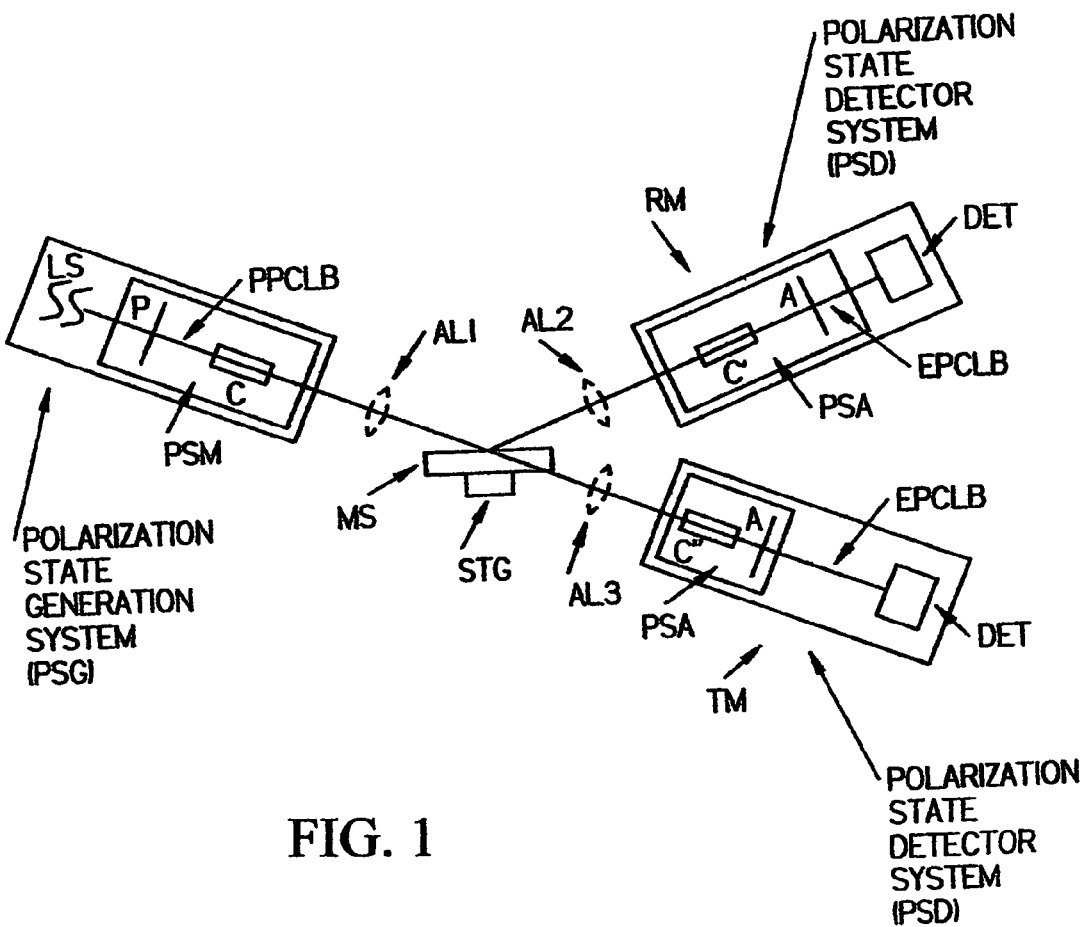
FIG. 1 show a typical ellipsometer system.

FIG. 1 show a typical ellipsometer system. Indicated are a Polarization State Generation System (PGS), and Polarization State Detector Systems (PSD) in both Reflective and Transmission Mode orientations. Note that the Polarization State Generation System (PGS) comprises a Source (LS) of electromagnetic radiation, a Polarizer (P) and optionally a Compensator (C) which act on beam (PPCLB) to impose a known polarization state thereupon. A Lens (AL1) can be present to focus the beam (PPCLB) onto a Sample (MS) which is set atop a Stage (STG). The Polarization State Detector Systems (PSD) each optionally comprise a Compensator (C') (C'), and Analyzer (A) and a Data Detectro (DET) which intercepts an Analyzed baem (EPCLB). Also shown are optional Lenses (AL2) and (AL3) which can be applied to re-collimate electromagnetic radition, when optional Lens (AL1) is present, after interaction with the Sample (MS). In use a beam of electromagnetic radiation in a known polarization state is caused to interact with a sample system, and after said interaction the polarization state is detected. Change in said Polarization State is determinative of well known ellipsometric PSI (Ψ) and ellipsometric DELTA (Δ), which are related to orthogonal components of said beam $r_p$ and $r_s$ as:

$\rho = r_p/r_s = \text{Tan}(\Psi)\exp^{i\Delta}$

Figure 2:
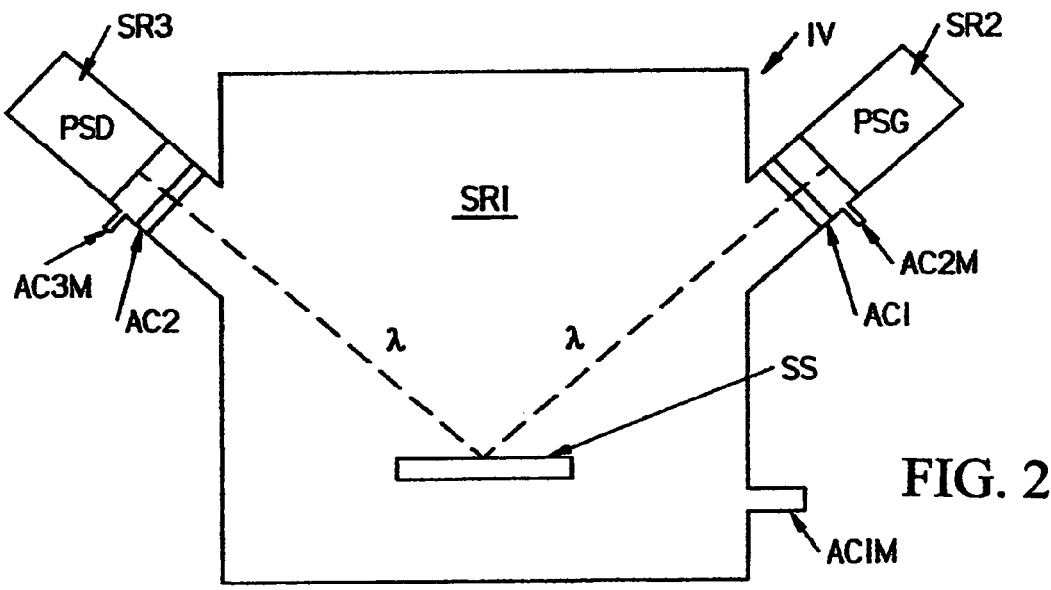
FIG. 2 shows the presence of an ellipsometer system in an environmental control chamber.

FIG. 2 shows the presence of an ellipsomete system in an Environmental Control Chamber (IV), which can be applied in in-situ work. Co-ordinated with FIG. 1, note the presence of a Polarization State Generation System (PGS), and a Polarization State Detector System (PSD) oriented in Reflective Mode. Note that the Sample (S) can be present in a common intenal area (SRI) with said Polarization State Generation System (PGS), and a Polarization State Detector System (PSD), or the (PSG) and (PSD) can be in separately controled regions, with Windows (AC2) and (AC1) acting as separation barriers which are transparent to wavelengths used. Note that (AC1M) (AC2M) and (AC3M) are indicated as means to control the atmosphere inside associated regions. FIG. 2 is shown as the disclosed invention utilizes a large range of wavelengths, and wavelengths in the (IR) and (VUV) ranges, for instance, are absorbed by water vapor. Means to avoid said problem is therefore necessary.

Figure 3A:
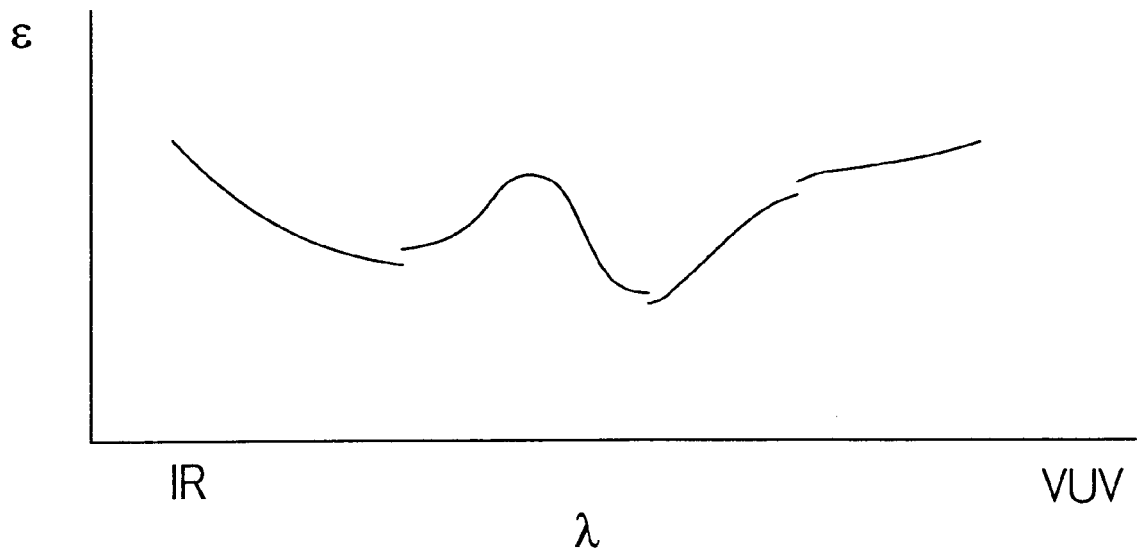
FIGS. 3a and 3b demonstrate postulated Dielectric Function results obtained over a large range of wavelengths conventionally, and by present invention methodology, respectively.
Figure 3B:
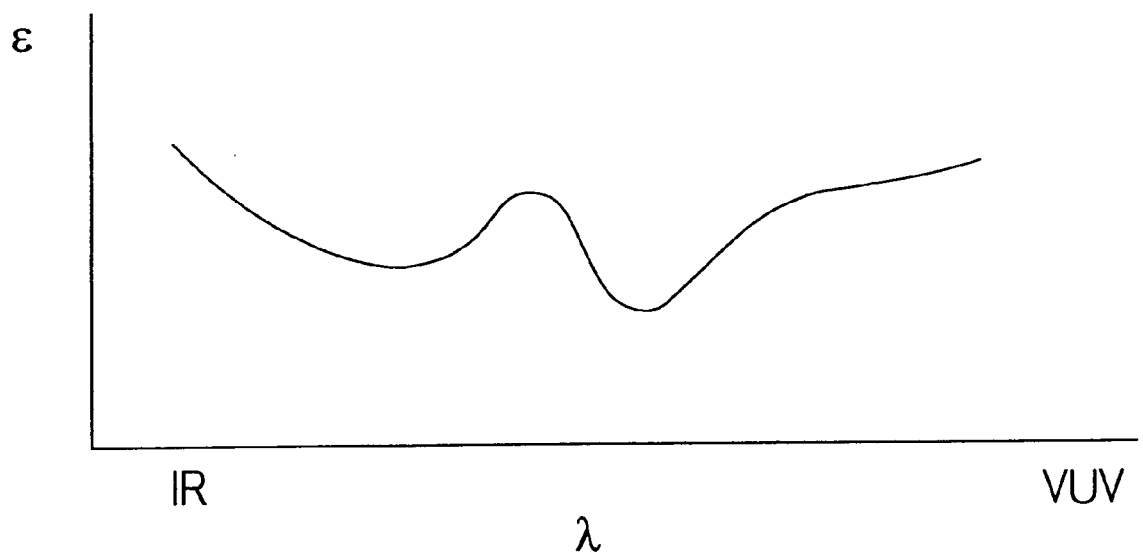

FIGS. 3a and 3b demonstrate a postulated Dielectric Function over a large range of wavelengths. Note that the FIG. 3a plot demonstrates jumps where different systems were used to obtain data. Typically reported data demonstrates such gaps as data from each system evaluated separately. FIG. 3b shows postulated results obtainable by practice of the disclosed invention wherein a single regression for all data over the entire range of wavelengths is subjected to a single regression procedure onto a mathematical model. The jumps in the locus of the FIG. 3b plot are smoothed to provide a more realistic result.

Said Oscillator Structures, and more, are described in the J.A. Woollam Co. WVASE32 Manual and Addendums, which are incorporated by reference herein. (WVASE32 is a-Registered Tradeamrk of the J.A. Woollam Co. Inc.).

Figure 4:
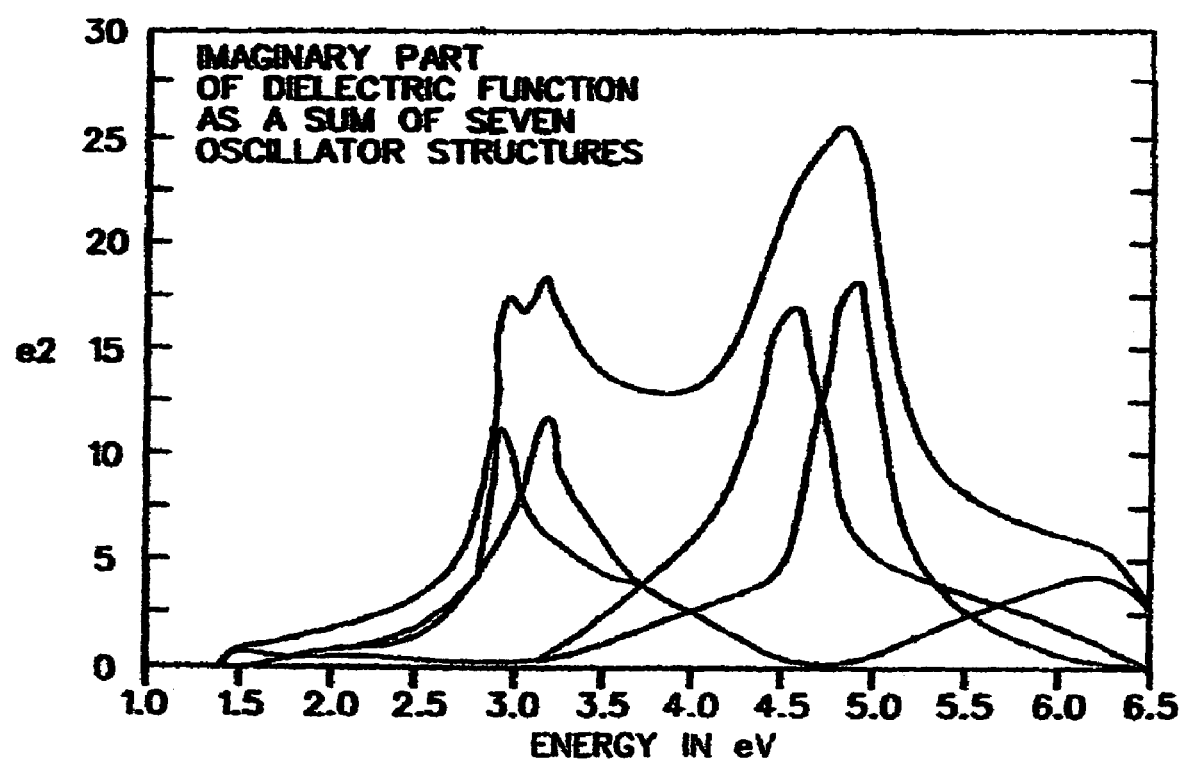
FIG. 4 show Oscillator Structures applied to model a Dielectric Function.

FIG. 4 demonstrates how placing Oscillator Structures appropriately in a Dielectric Function allows modeling it as a sum of said Oscillator Structures at each wavelength. The outer plot results from the sum of seven Psemi oscillators. Dielectric Function plots known over a Spectroscopic Range can be modeled by placing Oscillator Strurctures of appropriate shape at appropriate locations under, for instance, the imaginary part of thereof such that summation of their contributions at each wavelength results in said Dielectric Function. The Oscillator Structures are Kramers-Kronig consisant, hence modeling the Imaginary part allows calculation of the real part.

Example of Application of the J.A. Woollam Co GEMOSC™ Layer

As an example of application of the J.A. Woollam CO. GEMOSC™ Layer, which was mentioned in the Disclosure Section of this Specification, the following simple Analysis of a SiNx film is presented. Generally, the GENOSC approach is applicable to analysis of thin films which are, transparent in one wavelength range and absorbing in another, (eg. transparent at visible wavelengths but demonstrating;significant absorption at UV wavelengths). The approach is applicable to modeling:

$n(\lambda)+ik(\lambda)$
$e1(\lambda)+ie2(\lambda)$;

which expressions are mathematically identical

In that light it is disclosed that amorphous SiNx films are often transparent in the near-infrared (NIR) and throughout the most of the visible (VIS) spectra. Above the Bandgap, the UV of the $e2(\lambda)$ curve often demonstrates broad bulging curvature as can be modeled by a Tauc-Lorentz Dispersion function.

The Analysis Strategy for applying the GENOSC Layer is based in the realization that where a film is transparent over a portion of its measured spectral range, it is usually possible to accurately determine the film's thickness in that range. Further, once the film thickness is determined from one protion of a spectral range, it is often possible to determine the optical constants thereof over the entire measured spectral range. The strategy for analysis of sample systems using the J.A. Woollam CO. GEMOSC™ Layer is:

1. Determine the Thickness of the Layer

For instance, a film thickness can be determined in the NIR and VIS wavelength regions using a Cauchy or Sellmeier Optical Model.

2. Obtain Preliminary Optical Constants for the Entire Measured Spectral Region

Fix the Thickness, and possibly other fit parameters and obtain a preliminary set of Optical Constants from a Wavelength by Wavelength (eg. point by point), fit to data across the entire measured spectral range, then save the results.

3. Fit Tauc-Lorentz Oscillator to Step 2 Data Point by Point

Invoke the GENOSC Layer and Fit the defining parameters, of appropriate Oscillator Structure(s) appropriately positioned in the $e2(\lambda)$ plot, (eg. Amplitude (AM) and Broadening (BR)) of a Tauc-Lorentz Oscillator, to model the preliminary set of Optical Constants obtained in Step 2. The initial fit is acomplished via regression onto the $e2(\lambda)$ data only, and using initial conditions determined therereby in a fit to both $e1(\lambda)$ and $e2(\lambda)$ data.

4. Fit Thickness and Tauc-Lorentz Model Parameyers Simultaneously to the Ellipsometric Data Fit letting the Thickness float along with Oscillator Structure definging Parameters 5. Refine the Model Add refinements to the model in Step 4, such as surface roughness, grading, additional oscillator structures etc.).

6. Itterate

Repeat Steps 2-5 using the model developed in Step 5 as a starting model.

(It is noted that the terminology "Fit" indicates a mathematical procedure, such as squre error minimizing based-regression, wherein mathematical model parameters are assigned values so that calculations based thereon match the empirically obtained data being modeled).

Figures 5, 6A, 6B:
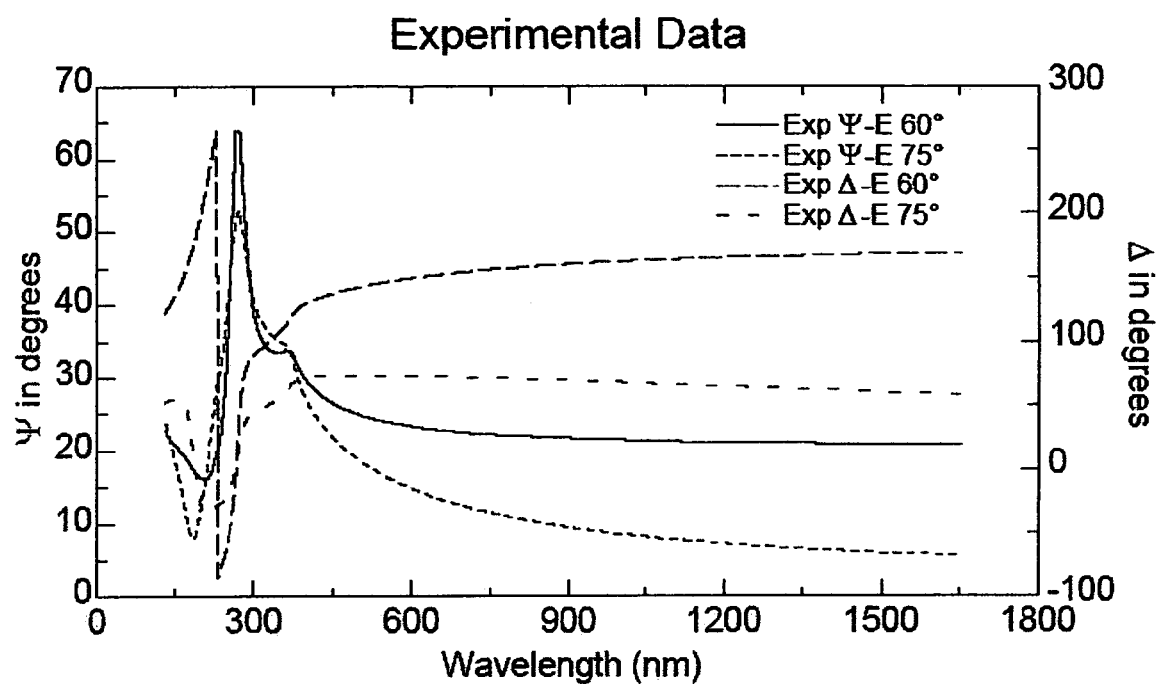
FIGS. 5, 6a, 6b and 7a-7p demonstrate application of the J.A. Woollam CO. GENOSC™ Layer to evaluate thin layer optical constants with Kramers-Kronig consisant Dispersion Relationships.
Figure 7A:
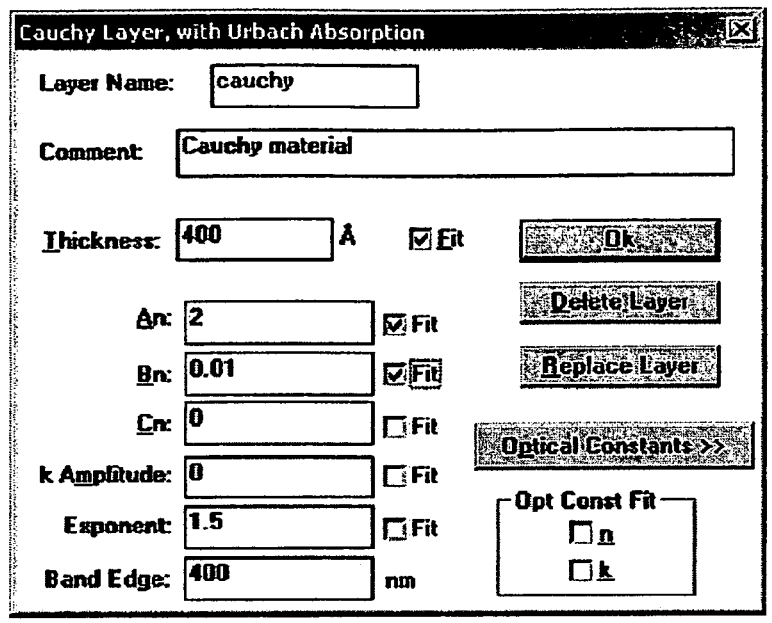
Figure 7B:
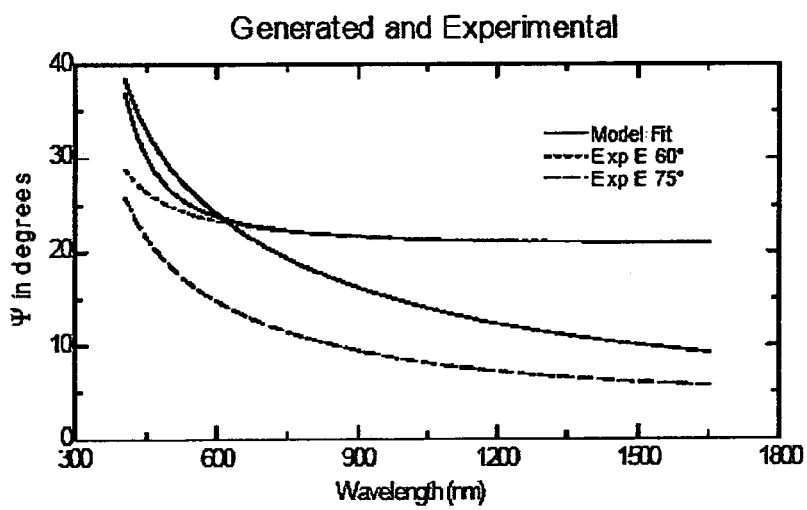
Figure 7C:
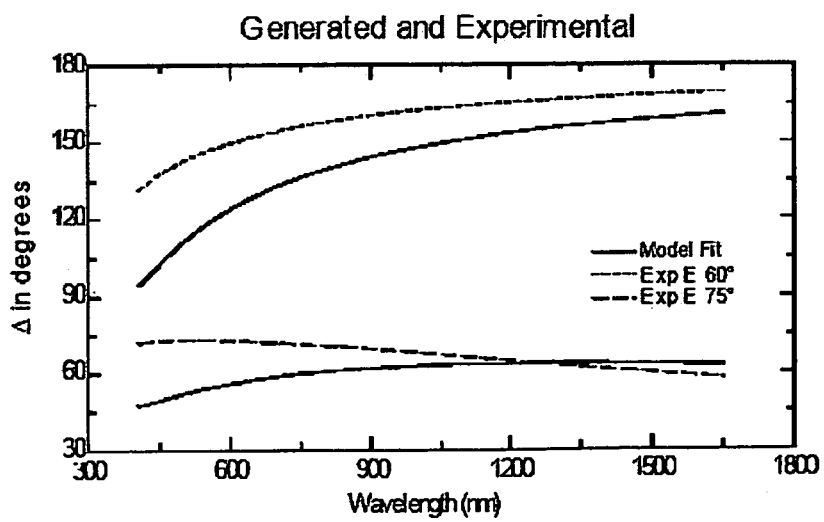

Turning now to FIG. 5, there is shown, for 60 and 75 degrees Angle-of-Incidence, experimentally obained ellipsometric PSI ($\Psi$) and DELTA ($\Delta$) data over a spectroscopic range of 190 to 1650 nm for the sample system of interest in this demonstration which comprises a SiNx film on a Silicon Substrate. With said data available, It is possible to determine the Thickness of the SiNx Film using a Cauchy or Sellmeier Layer. It is noted that over the Wavelength Range of from 400 to 1700 nm, the film is substantially transparent, and Thickness is determined utilizing this range. Using the J.A. Woollam Co. WVASE32 Software a Sample Model is developed comprising a Silicon Substrate with a Cauchy or Sellmier Layer atop thereof. Said WVASE32 Software provides a separate Cauchy Layer, but the Sellmeier Layer is accessed via the GENOSC Layer. FIGS. 6a and 6b show how said Models appear on a WVAS32™ Screen. Where the Cauchy Model is used FIG. 7a demonstrates a WVAS32™ Screen which allows identifying what parameters are fit. Note that Anc and Bnc, which are Cauchy Parameters, and Thickness are fit, with initial values therefore being set to 2, 0.01 and 400 Angstroms, respectively. Before the regression the results are as shown in FIGS. 7b and 7c.

FIGS. 7d and 7e show Plots of PSI ($\Psi$) and DELTA ($\Delta$) after the regression, and FIG. 7f demonstrates that the Film Thickness is evalutated as 224.39 Angstroms. Note that the fit to arrive at said Thickness was over the range of about 300 to 1800 nm, the region in which the Film was transparent. Similar results were obtained using the Sellemier (GENOSC Layer) approach but are not shown.

Figure 7G:
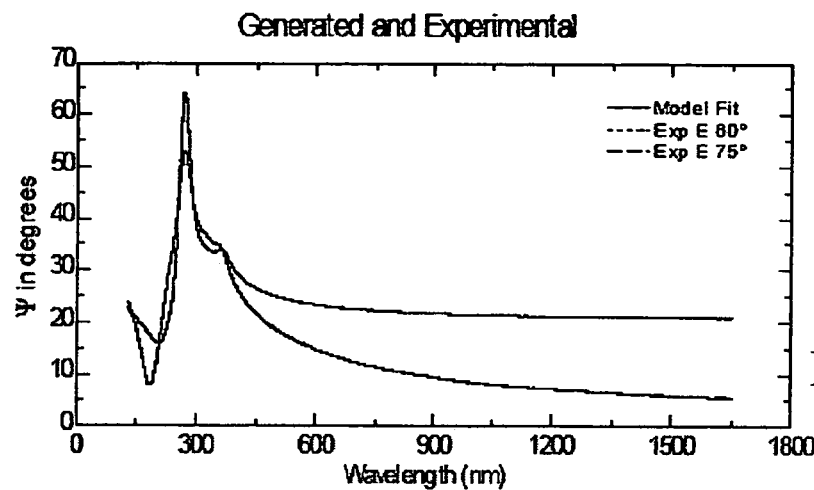
Figure 7H:
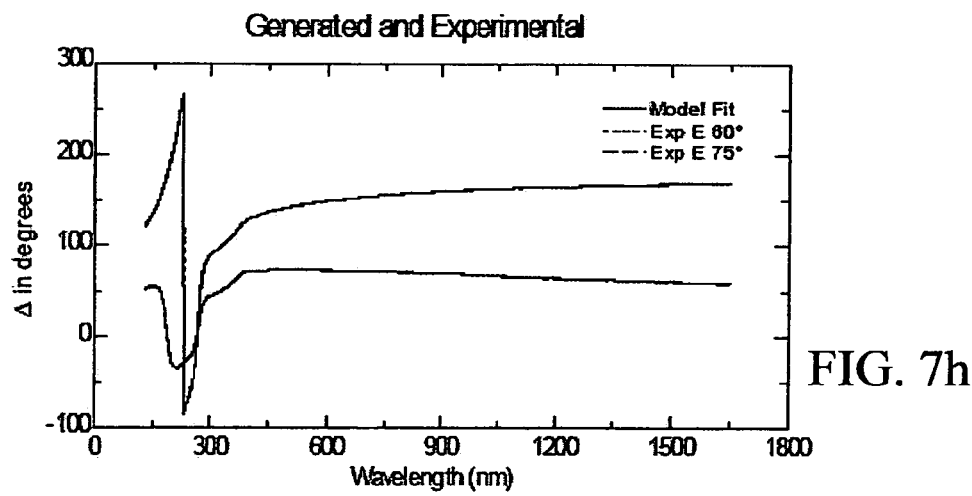
Figure 7I:
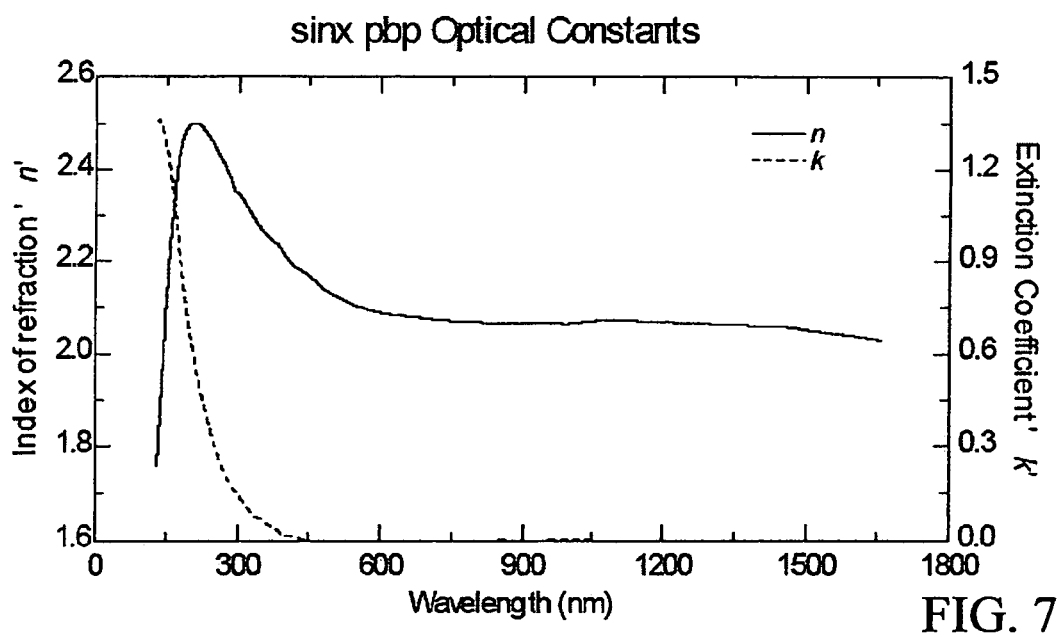

With the Thickness evaluated, the next step is to fix the value of the Thickness, and then while still utilizing the same Model, (eg. Cauchy or Sellmeier Model), do a point by point fit beginning at the Long Wavelength and working toward the shorter Wavelength portion of the wavelength range, including below 300 nm where FIG. 5 shows the results get more complex. This can be done all at once, but usually is done is a sequence of steps, each projecting a bit further into the range where the results are more complex, (eg. below 300 nm in FIG. 5). If the Point-by Point fit is attempted over the entire range of wavelengths all at once it often occurs that a good fit is not realized in the more complex region of the wavelength spectrum, (eg. below 300 nm in FIG. 5), but where small portions of the more complex wavelength spectrum region are sequentially incorporated each of which project further and further into the more complex region, a good fit can be achieved over the entire wavelength spectrum. FIGS. 7g and 7h demonstrate results obtained by the described Point by Point Procedure, and FIG. 7i shows the Optical Constants (n) and (k) whcih can be extracted therefrom. Said Optical Constants, determined as described, are then saved.

Figure 7J:
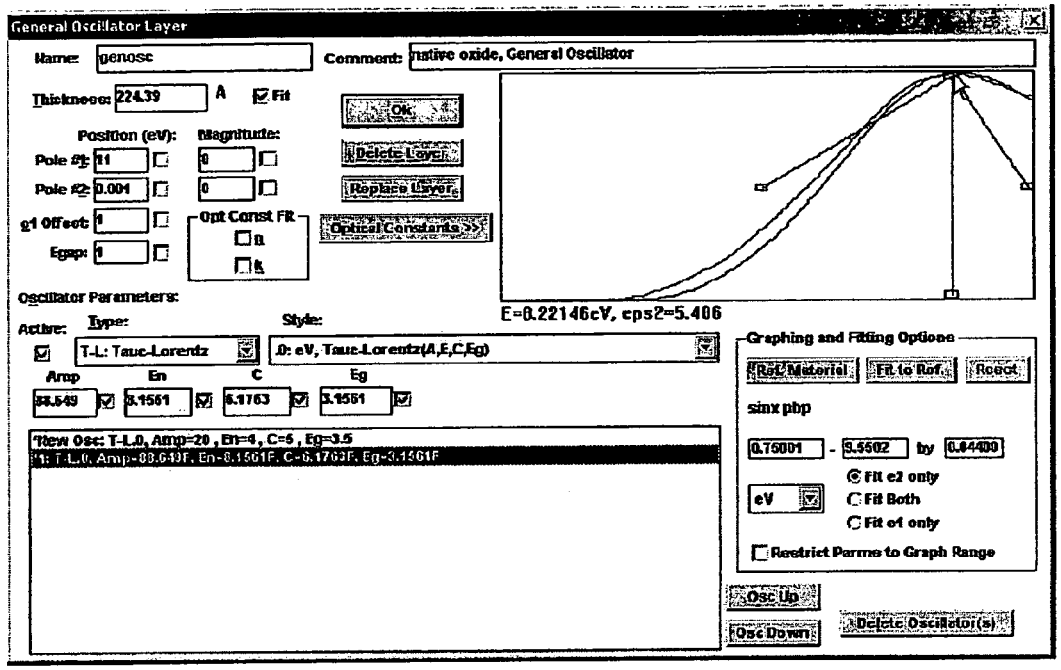
Figure 7K:
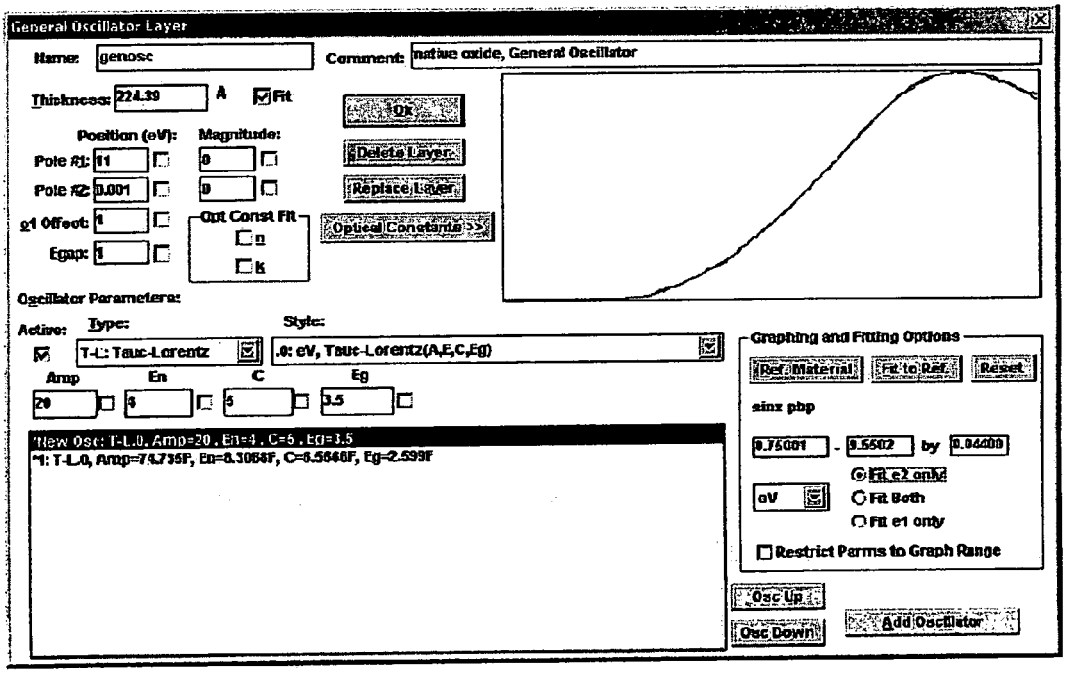
Figure 7L:
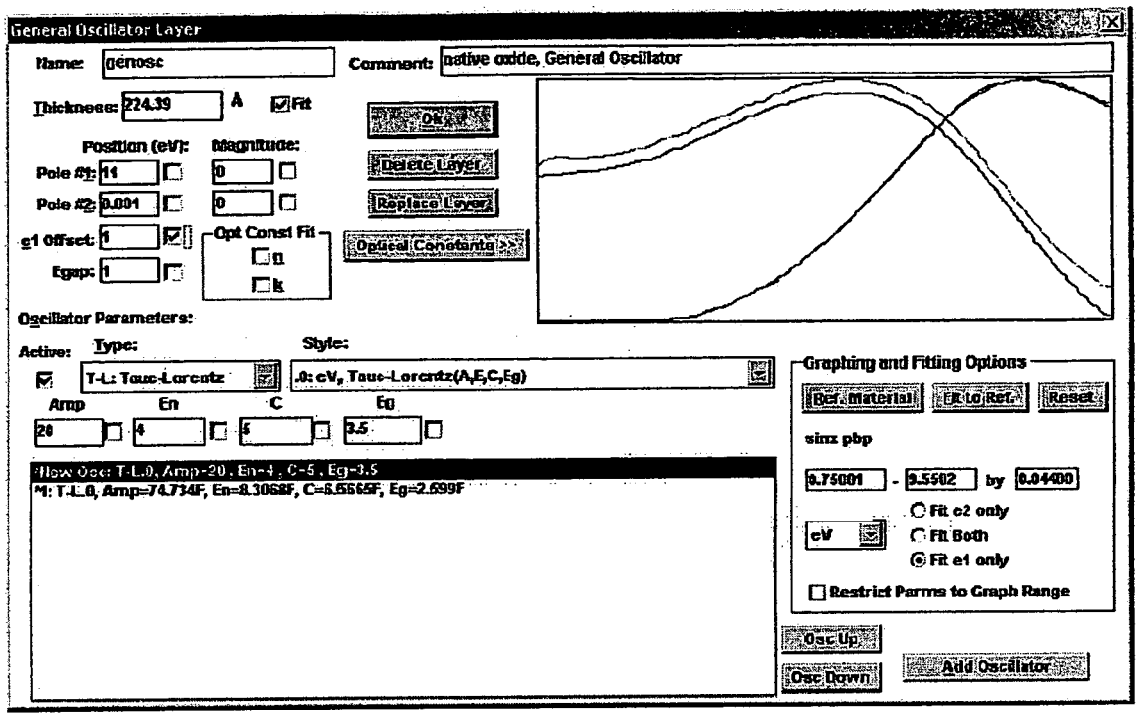
Figure 7M:
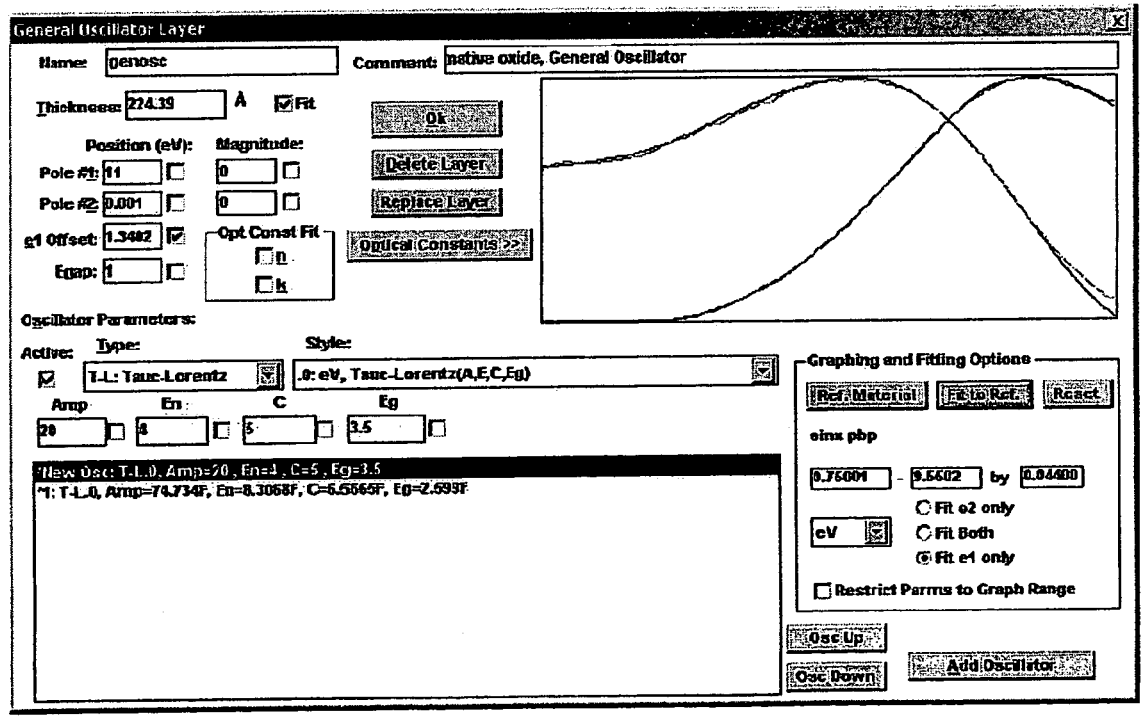
Figure 7N:
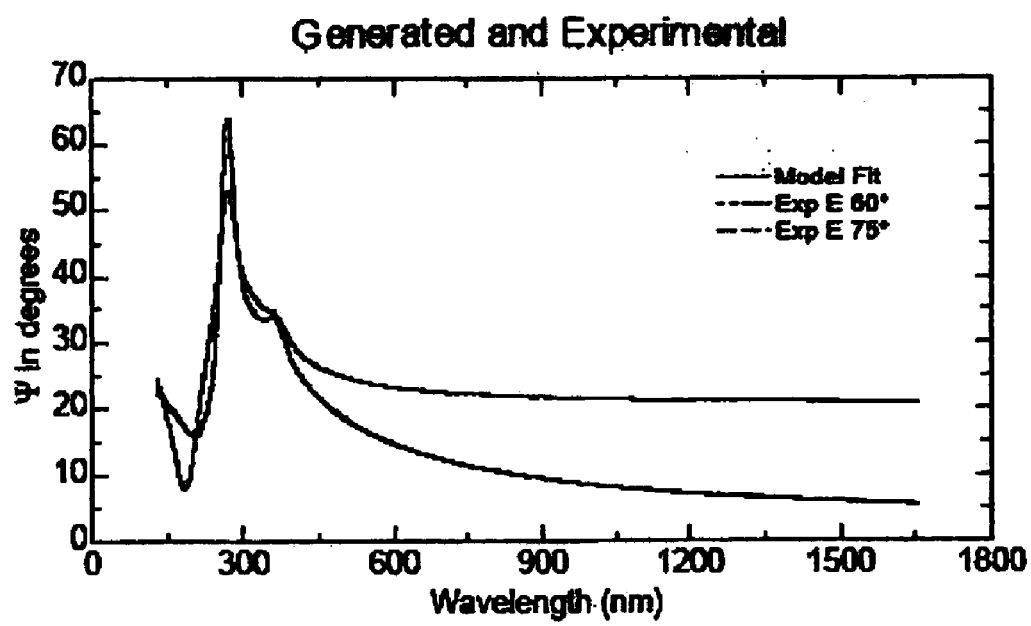
Figure 7O:
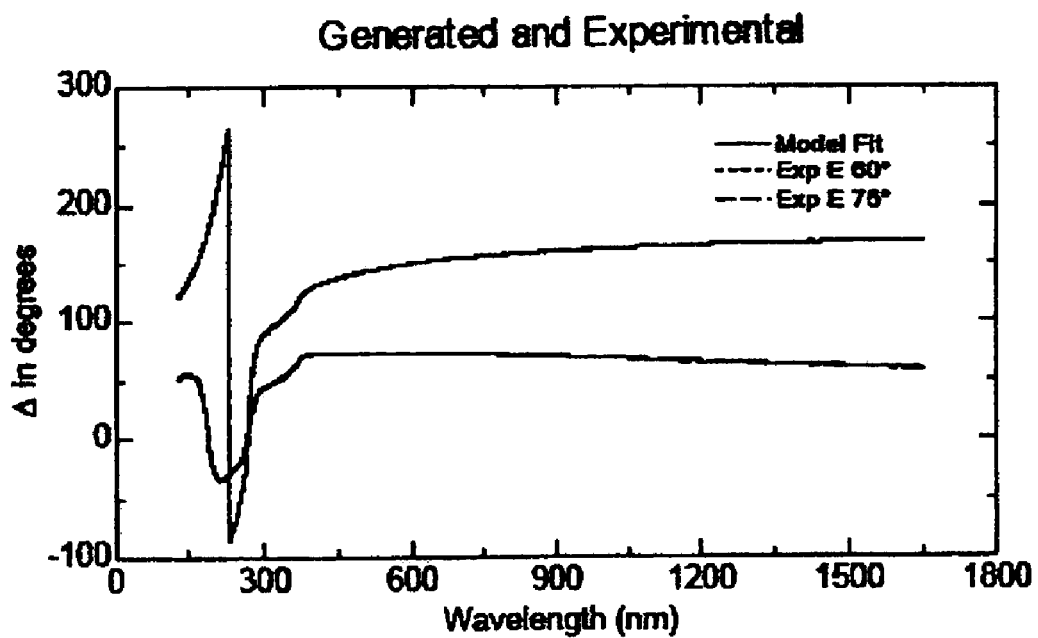

To this point the work has utilized a Cauchy or Sellemier Dispersion Model. At this point the procedure, changes and replaces the Cauchy Layer with a GEMOSC™ Layer. If the Sellemier Dispersion Model was utilized, this step involves replacing it with a new GEMOSC™ Layer that comprises at least one Kronig-Krammer Oscillator Sturcture. In either case, the procedure continues with positioning said at least one Kronig-Krammer Oscillator Stucture in the Imaginary Part (e2) of the Dielectric Function. FIGS. 7j and 7k show WVASE32 Screens during application of a Tauc-Lorentz Oscillator before and after, respectively a fit is performed, respectively, to the Imaginary Part (e2) of the Dielectric Function. FIGS. 7i and 7m demonstrate the before and after WVASE32 Screen results achieved by simultaneously fitting both the Kronig-Krammer related Real (e1) and Imaginary (e2) parts of the Dielectric Function, using results obtained by fitting the Imaginary part (e2) as starting values. FIGS. 7n and 7o show the PSI ($\Psi$) and DELTA ($\Delta$) corresponding the the FIGS. 7i and 7m plots.

The procedure continues by performing a global fit of the Tauc-Lorentz Oscillator and Film Thickness to the data. The results appear very similar to those in FIGS. 7n and 7o, but the Fit Parameter values are slightly change, such as the Thickness value is evaluated as 223.75 Angstroms.

Figure 7P:
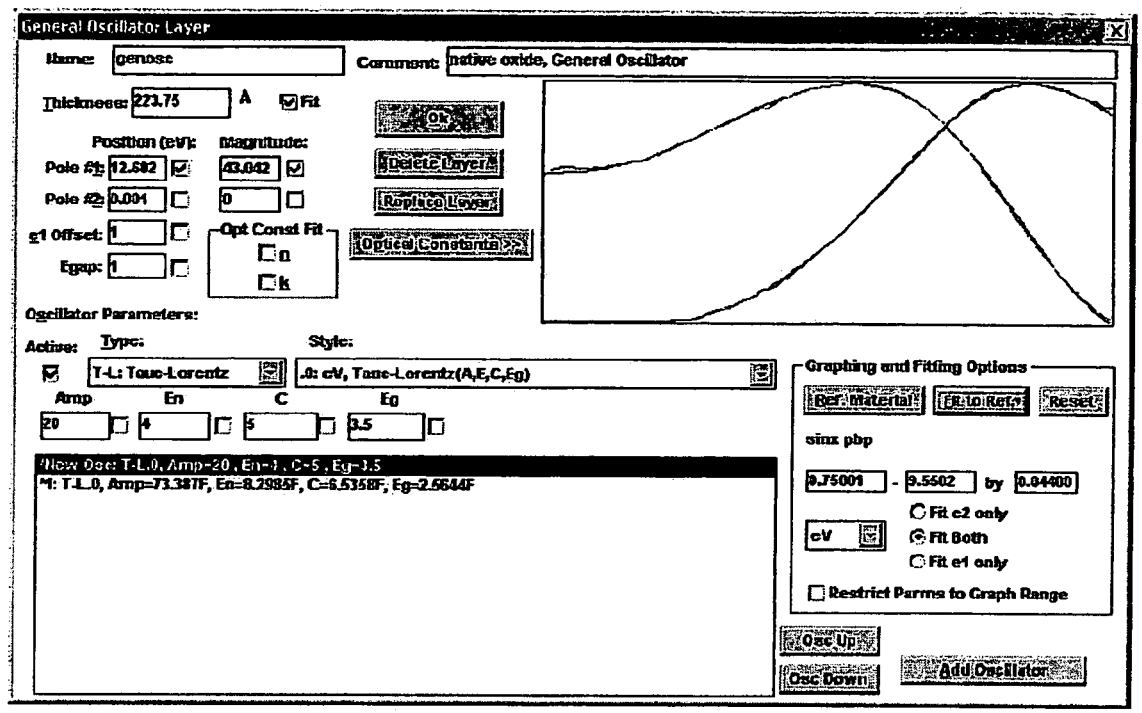

The Model achievd in this example is already very good, however, close inspection of the wavelength region below about 245 nm indicates some descrepency between experimental data and model fit in the PSI ($\Psi$) data. Further, close inspection of e1 data in FIG. 7l shows divergence between experimental data and results derived from the model at the longer wavelengths. Addition of a Pole has been found to minimize said descrepency. The GEMOSC™ Layer allows addition of a Pole and when starting values therefore are set to 1lev and a Magnitude of 1.0, and a fit to e1 and e2 data performed, FIG. 7p shows improved fit as compared to the fit in FIG. 7l. With this done, the GENOSE™ Layer can be closed and another Normal Global Fit peformed to provide slightly better PSI ($\Psi$) and DELTA ($\Delta$) plots, which actually look very much like the plots in FIGS. 7n and 7o.

The GEMOSC™ Procedure can be subjected to a second and additional itterations if results indicate. Further, it should be understood that the demonstrated GENOSE™ procedure was for a simple case where one Tauc-Lorentz Oscillator Structure was sufficient to fit the data. More usual situations require the simultaneous application of a plurality of Oscillator Structures.

It is to be appreccated that the terminology "Sample System" as used in this Specification can mean a Substrate perse., or a Substrate with one or more Thin Films on its surface, and the terminology "Optical Constants" can refer to those of a Substrate per se. or to those of one or more Thin Films.

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the Claims.

We claim:

1. A method of determining the optical constants of a sample system comprising a substrate with at least one thin film on a surface thereof, utilizing a spectroscopic beam of electromagnetic radiation, comprising the steps of:
  a) obtaining ellipsometric data over a spectroscopic range between FIR and VUV wavelengths and displaying said data as an ellipsometric parameter vs. a parameter which varies with wavelength, said plot being characterized by a range corresponding to longer wavelengths in which said sample system is substantially transparent and typically demonstrates effects of interference resulting from reflections from the surface and at least one thin layer interface therebelow, and a range corresponding to shorter wavelengths in which said plot demonstrates dominant absorption effects;
  b) proposing a mathematical model of said sample system, said mathematical model comprising parameters which allow determining a selection from the group consisting of:
    refractive index and extinction coefficient, and
    real and imaginary parts of the dielectric function;
  and generating data corresponding to the data in step a and effectively displaying said generated data from said mathematical model;
  c) selecting a range in said plots in which absorption effects are not dominant, and simultaneously performing regression over said range to set parameter values in said mathematical model to values such that the plots of the obtained and generated data are substantially the same;
  d) setting the range of wavelengths to a selection from the group consisting of:
    the entire obtained spectroscopic range; and
    a portion of the spectroscopic range including the range in which absorbtion effects are dominant and a portion of the spectroscopic range in which absorption effects are not dominant;
  then performing a selection from the group consisting of:
    a point by point fit begining in the range in which absorption effects are not dominant, such that refractive index and extinction coefficients or real and imaginary parts of the dielectric function are determined over said selected spectroscopic range; and
    a simultaneous global regression using wavelengths both inside and outside the spectroscopic range in which absorption effects are not dominant, such that refractive index and extinction coefficients or real and imaginary parts of the dielectric function are determined over said selected spectroscopic range; and
  e) diplaying at least some determined optical constant data over at least a portion of said spectroscopic range.

2. A method of determining the optical constants of a sample system comprising a substrate with at least one thin film on a surface thereof, utilizing a spectroscopic beam of electromagnetic radiation, comprising the steps of:
  a) obtaining ellipsometric data over a range of spectroscopic wavelengths between FIR to VUV and displaying said data as an ellipsometric parameter vs. a parameter which varies with wavelength, said plot being characterized by a range corresponding to longer wavelengths in which said sample system is substantially transparent and a range corresponding to shorter wavelengths in which the plot demonstrates the effects of absorption;
  b) proposing a mathematical model of said sample system, said mathematical model comprising parameters allowing determining a selection from the group consisting of:
    refractive index and extinction coefficient; and
    real and imaginary parts of the dielectric function;
  as parameters, and generating data corresponding to the data in step a from said mathematical model, and effectively displaying said generated data with said obtained ellipsometric data over the spectroscopic range;
  c) selecting a spectroscopic range of wavelengths in which absorption effects are not dominant and simultaneously performing regression over said spectroscopic range to set parameters in said mathematical model to values such that the plots of the obtained and generated data are substantially the same;
  d) fixing the value of at least one parameter determined in step c, and setting the spectroscopic range to the full range of the obtained data then performing a selection from the group consisting of:
  a point by point fit begining in the transparent range such that refractive index and extinction coefficients or real and imaginary parts of the dielectric function are determined over said spectroscopic range; and
  a simultaneous global regression on wavelengths both inside and outside the spectroscopic range in which absorption effects are demonstrated such that refractive index and extinction coefficients or real and imaginary parts of the dielectric function are determined over said selected spectroscopic range;
  a simultaneous global regression on wavelengths both inside and outside the spectroscopic range in which absorption effects are demonstrated such that refractive index and extinction coefficients or real and imaginary parts of the dielectric function are directly determined over said selected spectroscopic range, said global regresion serving to evaluate parameters in dispersion models, at least one of which is selected from the group consisting of:
  Cauchy;
  Cauchy+Urbach absorption;
  Selimejer Oscillator, (zero broadened);
  Lorentz Oscillator;
  Gaussian Oscillator;
  Harmonic Oscillator;
  Drude Oscillator;
  Tauc-Lorentz Oscillator;
  Cody-Lorentz Oscillator;
  Tanguay;
  Ionic Oscillator;
  TOLO;
  Gauss-Lorentz Oscillator;
  Gauss-Lorentz Oscillator Asymetric Doublet (Glad) Oscillator;
  Herzinger-Johs Parametric Semiconductor Oscillator Model;
  Psemi-Eo Oscillator;
  Critical Point Parabolic band (CPPB);
  Adachi Oscillator Model;
  Pole; and
  e) diplayinci at least some determined optical constant data over at least a portion of said spectroscopic range.

3. A method of determining the optical constants of a sample system comprising a substrate with at least one thin film on a surface thereof, utilizing a spectroscopic beam of electromagnetic radiation, comprising the steps of:
  a) obtaining ellipsometric data over a range of spectroscopic wavelengths between FIR to VUV and displaying said data as an ellipsometric parameter vs. a parameter which varies with wavelength;
said plot being characterized by a range corresponding to longer wavelengths in which said sample system is substantially transparent and typically demonstrates interference resulting from reflections from the surface and at least one thin layer interface therebelow, and a range corresponding to shorter wavelengths in which the plot demonstrates dominant effects of absorption;
  b) proposing a mathematical model of said sample system, said mathematical model comprising parameters allowing determining a in the selection from the group consisting of:
    refractive index and extinction coefficient;
    real and imaginary parts of the dielectric function;
as fit parameters, and generating data corresponding to the data in step a from said mathematical model and effectively displaying said generated data with said obtained ellipsometric data over the spectroscopic range;
  c) selecting a range of wavelengths in which absorption effects are not dominant and simultaneously performing regression over said range of wavelengths to set parameter values in said mathematical model to values such that the plots of the obtained and generated data are substantially the same;
  d) fixing the value of at least one parameter obtained in step c, and setting the range of wavelengths to include at least some the obtained data range in which absorption is dominant, and setting parameters allowing determination of a selection from the group consisting of:
    refractive index and extinction coefficient; and
    real and imaginary parts of the dielectric function;
as fit parameters, then performing a point by point fit begining in the range of wavelengths wherein absorption is not dominant, such that refractive index and extinction coefficients or real and imaginary parts of the dielectric function are determined over at least a portion of the range of the obtained data wherein absorption effects are dominant; and
  e) diplaying at least some determined optical constant data over at least a portion of said spectroscopic range.

4. A method as in claim 3, in which step d is performed at least one additional time with the range of wavelengths set to include more of the obtained data range in which absorption effects are not dominant and in which interference effects are present in the obtained data.

5. A method as in claim 4, in which step d is performed at least one additional time with the range of wavelengths is set to include yet more of the obtained data range in which absorption effects are dominant.

6. A method as in claim 3, in which step d is performed at least one additional time with the range of wavelengths is set to include the entire obtained data range.

7. A method as in claim 1, 2 or 3 in which the mathematical model comprises a Cauchy function to represent the thin film.

8. A method as in claim 1, 2 or 3 in which ellipsometric data is obtained at at least two angles of incidence.

9. A method as in claim 1, 2 or 3 which further comprises saving determined optical constants over the entire range of wavelengths, and replacing the mathematical model of the thin layer with a mathematical model which allows fitting the refractive index or imaginary part of the dielectric function with mathematical dispesion model, effectively plotting said parameters, fitting the effective plot with at least one mathematical dispersion model and performing a regression to evaluate parameters in said mathematical dispersion model.

10. A method as in claim 1, 2 or 3 which further comprises saving determined optical constants over the entire range of wavelengths, and replacing the mathematical model of the thin layer with a mathematical model which allows fitting the refractive index and extinction coefficient or the real and imaginary parts of the dielectric function with mathematical dispersion models, plotting said refractive index or real part of the dielectric function and fitting said refractive index or imaginary part of the dielectric function with at least mathematical dispersion model, and performing a regression to simultaneously evaluate refractive index and extinction coefficient or real and imaginary parts of the dielectric function parameters in said mathematical dispersion model.

11. A method as in claim 1, 2 or 3 which further comprises saving determined optical constants over the entire range of wavelengths, and replacing the mathematical model of the thin layer with a mathematical model which allows fitting the refractive index or the real part of the dielectric function with mathematical dispersion models, plotting said refractive index or real part of the dielectric function and fitting said refractive index or real part of the dielectric function with at least one mathematical dispersion model and performing a regression to evaluate parameters in said mathematical model, in which at least one said dispesion model is selected from the group consisting of:
- Cauchy;
- Cauchy+Urbach absorption;
- Sellmeier Oscillator, (zero broadened);
- Lorentz Oscillator;
- Gaussian Oscillator;
- Harmonic Oscillator;
- Drude Oscillator;
- Tauc-Lorentz Oscillator;
- Cody-Lorentz Oscillator;
- Tanguay;
- Ionic Oscillator;
- TOLO;
- Gauss-Lorentz Oscillator;
- Gauss-Lorentz Oscillator Asymetric Doublet (Glad) Oscillator;
- Herzinger-Johs Parametric Semiconductor Oscillator Model;
- Psemi-Eo Oscillator;
- Critical Point Parabolic band (CPPB);
- Adachi Oscillator Model;
- Pole.

12. A method as in claim 1, 2 or 3 which further comprises saving determined optical constants over the entire range of wavelengths, and replacing the mathematical model of the thin layer with a mathematical model which allows fitting the refractive index and extinction coefficient or the real and imaginary parts of the dielectric function with mathematical dispersion models, plotting said refractive index or real part of the dielectric function and fitting said refractive index or real part of the dielectric function with at least one mathematical dispersion model, and performing a regression to simultaneously evaluate refractive index and extinction coefficient or real and imaginary parts of the dielectric function parameters in said mathematical model, in which at least one said dispesion model is selected from the group consisting of:
- Cauchy;
- Cauchy+Urbach absorption;
- Sellmeier Oscillator, (zero broadened);
- Lorentz Oscillator;
- Gaussian Oscillator;
- Harmonic Oscillator;
- Drude Oscillator;
- Tauc-Lorentz Oscillator;
- Cody-Lorentz Oscillator;
- Tanguay;
- Ionic Oscillator;
- TOLO;
- Gauss-Lorentz Oscillator;
- Gauss-Lorentz Oscillator Asymetric Doublet (Glad) Oscillator;
- Herzinger-Johs Parametric Semiconductor Oscillator Model;
- Psemi-Eo Oscillator;
- Critical Point Parabolic band (CPPB);
- Adachi Oscillator Model;
- Pole.

13. A method as in claim 1, 2 or 3 which further comprises including parameters in said mathematical model which characterize at least one selection from the group consisting of:
- surface roughness;
- optical constant grading;
- anisotropy;
- at least one interface layer;
- thin film composition, (EMA);

said thin film composition being characterized by at least one selection selected from the group consisting of;
- thin film porosity;
- alloy percentage;
- thin film crystalinity;
- depolarization factor.

14. A method as in claim 1, 2 or 3 which further comprises including parameters in said mathematical model which characterize thin film composition, said parameters being modeled by effective media approximation (EMA) utilizing at least one selection from the group consisting of:
- Lorentz-Lorenz;
- Maxwell-Garnett;
- Bruggeman;
- Linear.

15. A method as in claim 1, 2 or 3 which further comprises including parameters in said mathematical model which characterize sample system anisotropy.

16. A method as in claim 1, 2 or 3 which further comprises including parameters in said mathematical model which characterize at least one selection from the group consisting of:
- thin film non-uniformity;
- electromagnetic beam wavelength bandwidth spread;
- spread in electromagnetic beam angle of incidence.

17. A method as in claim 1, 2 or 3 which further comprises including parameters in said mathematical model which characterize sample system caused incoherent effects.

18. A method as in claim 1, 2 or 3 which further comprises including parameters in said mathematical model which characterize sample system caused incoherent effects based upon patterns being present thereupon and/or backside reflections.

19. A method as in claim 1, 2 or 3 which further comprises including parameters in said mathematical model which characterize at least one selection from the group consisting of:
- sample system caused rotary effects;
- magneto-optic effects;
- electro-optic effects;
- sample system temperature effects;
- sample system strain effects.

20. A method as in claim 1, 2 or 3 which further comprises selecting starting numbers for parameters in the mathematical model which are input to the regression procedure by a method that tests mean square error after a small number of itterations for a seqence of starting values.

21. A method of determining the optical constants of a sample system comprising a substrate with a thin film on a surface thereof, utilizing a spectroscopic beam of electromagnetic radiation, comprising the steps of:
  a) obtaining spectroscopic ellipsometric data for said sample system at at least one angle of incidence by causing a spectroscopic beam of electromagnetic radiation including wavelengths from at least two ranges selected from:
    RADIO
    MICRO FIR;
IR;
NIR-VIS-NUV;
UV;
DUV; and
VUV;
EUV;
XRAY;
to interact with said sample system and enter a detector;
b) determining a range of wavelengths over which said thin film is substantially transparent and determining the thickness of said thin film utilizing ellipsometric data obtained in said region by applying a Cauchy or Sellmeier optical model and a square error minimizing regression to evaluate parameters therein;
c) fixing the thickness determined in step b, and obtaining a preliminary set of optical constants comprising:
$(e1(\lambda)+ie2(\lambda))$
by point by point fitting to data across the entire measured spectral range, and saving the resulting data;
d) while maintaining thickness fixed, applying at least one mathematical dispersion model to said saved results and evaluating parameters therein via regression onto the $e2(\lambda)$ data only,
e) while maintaining thickness fixed and using the results obtained in step d as initial conditions, performing a regression onto $e1(\lambda)$ and $e2(\lambda)$ data;
f) applying a global regression onto at least $e2( )$ data to fit all parameters, including thickness, over the entire spectral range;
g) modifying the mathematical model and repeating steps a-f at least once; and
h) diplaying at least some determined optical constant data over at least a portion of said spectroscopic range.

22. A method as in claim 1 or 2 or 3 or 21 in which the obtained ellipsometric data is obtained at a multiplicity of wavelengths and the optical model parameters which characterize the outermost layer(s) are refractive index and extinction coefficient vs. wavelength, and in which the method further comprises:
fitting said optical model parameters with at least one mathematical dispersion which is selected from the group consisting of:
Cauchy;
Cauchy+Urbach absorption;
Sellmeier Oscillator, (zero broadened);
Lorentz Oscillator;
Gaussian Oscillator;
Harmonic Oscillator;
Drude Oscillator;
Tauc-Lorentz Oscillator;
Cody-Lorentz Oscillator;
Tanguay;
Ionic Oscillator;
TOLO;
Gauss-Lorentz Oscillator;
Gauss-Lorentz Oscillator Asymetric Doublet (Glad) Oscillator;
Herzinger-Johs Parametric Semiconductor Oscillator Model;
Psemi-Eo Oscillator;
Critical Point Parabolic band (CPPB);
Adachi Oscillator Model;
Pole.

23. 3 A method as in claim 1 or 2 or 3 or 21 in which the sample system is comprised of at least one selection from the group consisting or:
Material with High or Low Extinction Coefficient (K);
Material with High or Low Refractive Index (N);
Metal;
Semimetal;
Semiconductor;
Insulator;
Transparent Oxide;
Liquid;
Fluid;
Oils;
Lubricant;
Biological material;
Nucleic Acid;
DNA &/or RNA;
Protein;
Amino Acid;
Carbohydrate;
Wax ;
Fat;
Lipid;
Plant material;
Animal material;
Fungi material;
Microbe material;
Tissue;
Condensate;
Combination Solid and Liquid &/or Gas;
Liquid Crystal;
Porous material;
Alloy;
Compound;
Composite;
Ceramic;
Polymer;
Fiberous material;
Wood containing material;
Paper containing material;
Plastic;
Crystaline material;
Amorphous material;
Polycrystaline Material;
Glassy material;
Homogeneous material;
Inhomogeneous material;
Superlattice;
Superconductor;
Lamgmuir-Blodgett material;
Monolayer;
Fractional Monolayer;
Multi layer;
Samples comprising Quantum Dots &/or Wells;
Polymer;
Conjugated Polymer;
Films of any material on substrate of another material
Monoparticles;
Composites containing monopartixcles;
Nanomaterials;
Materials containing Nanomaterials;
Superlattices with Nanoparticles
combinations of the above.

24. A method as in claim 1 or 2 or 3 or 21 in which evaluation is achieved for at least one selection from the group consisting:
energy gap;
index of refraction;
growth rate;
etch rate;

thickness;
extinction coefficient;
carrier concentration;
alloy ratio;
critical point;
depolarization rate;
inhomogenuity;
grading;
anisotropy;
temperature;
crystalinity;
stress;
strain;
interface layer;
surface layers;
surface layer roughness;
interface roughness;
electro-optic coefficient;
magneto-optic coefficient;
chemical bond presence;
chemical bond strength;
combinations of the above.

25. A method as in claim 1 or 2 or 3 or 21 in which data obtained corresponds to at least one selection from the group consisting of:

reflection from sample system;
transmission through sample system;
monochromatic;
spectroscopic;
ellipsometric;
single sample system;
multiple sample system;
single angle of incidence;
multiple angles of incidence;
acquired from single instrument;
acquired from multiple instruments;
single sample system orientation;
multiple sample system orientations;
focused beams;
divergent beams;
unfocused beams;
in-situ;
ex-situ;
kerr magneto-optic;
kerr magneto-optic coincident with ellipsometric;
combinations of the above.

* * * * *